US010285958B2

(12) United States Patent
Willmann et al.

(10) Patent No.: US 10,285,958 B2
(45) Date of Patent: May 14, 2019

(54) GENOTYPE- OR PHENOTYPE-BASED DRUG FORMULATION

(71) Applicant: BAYER AKTIENGESELLSCHAFT, Leverkusen (DE)

(72) Inventors: Stefan Willmann, Düsseidorf (DE); Thomas Eiβing, Langenfeld (DE); Kristin Dickschen, Düsseidorf (DE)

(73) Assignee: BAYER AKTIENGESELLSCHAFT, Leverkusen (DE)

(*) Notice: Subject to any disclaimer, the term of this patent is extended or adjusted under 35 U.S.C. 154(b) by 0 days.

(21) Appl. No.: 14/403,823

(22) PCT Filed: May 27, 2013

(86) PCT No.: PCT/EP2013/060824
§ 371 (c)(1),
(2) Date: Nov. 25, 2014

(87) PCT Pub. No.: WO2013/178565
PCT Pub. Date: Dec. 5, 2013

(65) Prior Publication Data
US 2015/0174082 A1 Jun. 25, 2015

(30) Foreign Application Priority Data
Jun. 1, 2012 (EP) .................................. 12170401

(51) Int. Cl.
A61K 31/138 (2006.01)
G06F 19/12 (2011.01)

(52) U.S. Cl.
CPC ............ *A61K 31/138* (2013.01); *G06F 19/12* (2013.01)

(58) Field of Classification Search
None
See application file for complete search history.

(56) References Cited

U.S. PATENT DOCUMENTS

| 4,929,610 A | 5/1990 | Meier et al. |
| 5,541,067 A | 7/1996 | Otsuka |
| 6,048,857 A | 4/2000 | Ellinwood et al. |
| 7,169,813 B2 | 1/2007 | Formelli |
| 7,427,480 B2 | 9/2008 | Margus et al. |
| 7,805,282 B2 | 9/2010 | Casey et al. |
| 7,970,552 B1 | 6/2011 | Stefanon et al. |
| 8,024,128 B2 | 9/2011 | Rabinowitz et al. |
| 8,147,615 B2 | 4/2012 | Weber |
| 8,275,442 B2 | 9/2012 | Allison |
| 9,320,738 B2 | 4/2016 | Gruber et al. |
| 9,372,198 B2 | 6/2016 | Gonda |
| 9,417,221 B2 | 8/2016 | Varshney et al. |
| 2002/0012921 A1 | 1/2002 | Stanton |
| 2006/0264514 A1 | 11/2006 | Formelli |
| 2007/0122824 A1 | 5/2007 | Tucker et al. |
| 2009/0012921 A1 | 1/2009 | Bonnet et al. |
| 2009/0094059 A1 | 4/2009 | Coleman et al. |
| 2010/0011204 A1 | 1/2010 | Hubbard et al. |
| 2010/0153016 A1 | 6/2010 | Stefanon et al. |
| 2011/0010099 A1 | 1/2011 | Adourian et al. |
| 2011/0113002 A1 | 5/2011 | Kane et al. |
| 2012/0053157 A1* | 3/2012 | Kumar ............... A61K 31/4365 514/161 |
| 2012/0329762 A1* | 12/2012 | Kumar ................. C07D 513/04 514/161 |
| 2013/0259847 A1 | 10/2013 | Vishnudas et al. |
| 2015/0174082 A1 | 6/2015 | Willmann et al. |

FOREIGN PATENT DOCUMENTS

| EP | 0 207 451 A2 | 1/1987 |
| JP | S 62 5916 A | 1/1987 |
| JP | 2007 529494 A | 10/2007 |
| WO | 37/17948 A1 | 5/1997 |
| WO | 2006/130843 A1 | 12/2006 |
| WO | 2008/070463 A2 | 6/2008 |
| WO | 2011/072244 A1 | 6/2011 |

OTHER PUBLICATIONS

Uglietti, Alessia et al., Expert Opinion on Drug Metabolism & Toxicology (Sep. 4, 2012) vol. 8(10), pp. 1305-1314.*
Pauli-Magnus et al The Journal of Pharmacology and Experimental Therapeutics (2000) 293: 376-382.*
Ribeiro et al., Experimental Cell Research (Feb. 2014, published online May 24, 2013) vol. 321(2), pp. 288-296.*
Rofaiel et al. Pharmacogenomics and Personalized Medicine (2010) vol. 3, pp. 129-143.*
Mah et al. International Journal of Pharmaceutics (2013) 441: 433-440 [publ. online Nov. 2012].*
Eissing et al. Frontiers in Pharmacology, vol. 2(4),.*
Dickschen et al. Frontiers in Pharmacology, vol. 3(92),.*
International Search Report issued in corresponding application PCT/EP2013/060824 dated Aug. 5, 2013.
Blondeau et al; "In vitro killing of *Escherichia coli, Staphylococcus pseudintermedius* and Pseudomonas aeruginosa by enrofloxacin in combination with its active metabolite ciprofloxacin using clinically relevant drug concentrations in the dog and cat"; Veterinary Microbiology 155 (2012) pp. 284-290.
Vallée et al; "Individual and combined activities of clarithromycin and its 14-hydroxy metabolite in a murine model of Haemophilas influenzae infection"; Journal of Antimicrobial Chemotherapy (1991) 27, Suppl A; pp. 31-41.
Ross et al; "The components of VARA, a nutrient-metabolite combination of vitamin A and retinoic acid, act efficiently together and separately to increase retinyl esters in the lungs of neonatal rats"; The Journal of Nutrition, 2006, 136, 11; pp. 2803-2807.

(Continued)

*Primary Examiner* — Nyeemah A Grazier
(74) *Attorney, Agent, or Firm* — McBee Moore Woodward & Vanik IP, LLC

(57) ABSTRACT

The invention relates to a combination of two or more pharmaceutically active substances, of which at least one is a metabolic product ("metabolite") of the other ("parent substance"), wherein in particular the dosages thereof are selected such that genotypically or phenotypically related variability in the conversion of the parent substance to the metabolite in particular individuals is compensated for.

10 Claims, 15 Drawing Sheets

(56) References Cited

OTHER PUBLICATIONS

Martin et al; "In vitro activity of clarithromycin alone and in combination with ciprofloxacin or levofloxacin against *legionella* spp.: enhanced effect by the addition of the metabolite 14-hydroxy clarithromycin"; Diagn Microbiol & Infect Dis, 1997, 29, pp. 167-171.
Ahmad, et al; "Endoxifen, a new cornerstone of breast cancer therapy: demonstration of safety, tolerability, and systemic bioavailability in healthy human subjects"; Clinical Pharmacology & Therapeutics, vol. 88, No. 6, Dec. 2010, pp. 814-817.
Madlensky et al; "Tamoxifen metabolite concentrations, CYP2D6 genotype, and breast cancer outcomes"; Clinical Pharmacology & Therapeutics, 2011.
Hertz et al; "Tamoxifen and CYP2D6: a contradiction of data"; The Oncologist, 2012, 17, pp. 620-630.
Wu, et al; "Estimation of tamoxifen metabolite concentrations in the blood of breast cancer patients through CYP2D6 genotype activity score"; Breast Cancer Res Treat (2012) 133; pp. 677-683.
Ahmad A. et al, Clinical Pharmacology & Therapeutics, nature publishing group, vol. 88, No. 6, Jan. 12, 2010, pp. 814-817.pdf.
Irving et al. "Genotype-Guided Tamoxifen Dosing Increases Active Metabolite Exposure in Women With Reduced CYP2D6 Metabolism: A Multicenter Study", Journal of Clinical Oncology, vol. 29 No. 24 (Aug. 20, 2011) p. 3232-3239.
Zhang et al. Progress of Research in Tamoxifen and the Active Metabolite Endoxifen aHINESE Journal of Breast Disease, vol. 5, No. 4 (2011) P. 493-498.
1ETABOLITES [Iickschen et al. "Physiologically Based Pharmacokinetic Modeling of Tamoxifen and Its in Women of Different CYP2D6 Phenotypes Provides New Insight Into the Amoxifen Mass Balance", Frontiers in Pharmacology, (2012), vol. 3, Pp. 2-16.
Mayo Clinic, "Cancer: Tamoxifen's Power comes from Endoxifen," Science Daily, (2008).
VlUEDTER, et al., "Activity Levels of Tamoxifen Metabolites at the Estrogen Receptor and the Impact of Genetic Jolymorphisms of Phase I and Ii Enzymes on Their Concentration Levels in Plasma," Clinical Pharmacology and Therapeutics, (2011), vol. 89, No. 5: 709-717.
Lim, et al., "Impact of CYP2D6, CYP3A5, CYP2C9 and CYP2C19 polymorphisms on tamoxifen pharmacokinetics in Asian breast cancer patients," British Journal of Clinical Pharmacology, (2011), vol. 71, No. 5: 737-750.
Dickschen, et al., "P204 Overcoming CYP2D6-Mediated Tamoxifen Resistance: Phenotype-specific Tamoxifen-Endoxifen Combinations," The Breast 2251, S71-S120, S86 Poster Abstracts II (Mar. 2013).
Willmann, et al., "Integration of dissolution into physiologically-based pharmacokinetic models III: Pk-Sim," Journal of Pharmacy and Pharmacology, (2012), vol. 64: 997-1007.
Dickschen, et al., "PI-88," Clinical Pharmacology & Therapeutics, vol. 93, Abstracts-Supplement 1, p. S45-S46 (Feb. 2013).
Gad, S.C., "Active drug metabolites in drug development," Current Opinion in Pharmacology, (2003), vol. 3:98-100.
Rollas, Sevim, "In Vivo Metabolism in Preclinical Drug Development," Pharmaceutical Sciences Encyclopedia: Drug Discovery, Development, and Manufacturing, (2010), p. 3.
Fura, et al., "Discovering Drugs through Biological Transformation: Role of Pharmacologically Active Metabolites in Drug Discovery," J. Med. Chem., (2004), vol. 47, No. 18: 4339-4351.
Chen, et al., "Analytical Tools and Approaches for Metabolite Identification in Early Drug Discovery," Pharmaceutical Research, (2006), vol. 24, No. 2: 248-257.

\* cited by examiner

A: Loose combination of tamoxifen and endoxifen a) 20 mg TAM + 0 mg END (for CYP2D6 EMs and UMs)
b) + • 20 mg TAM + 1 mg END (for CYP2D6 IMs)
c) + ● 20 mg TAM + 3 mg END (for CYP2D6 PMs)

B: FDC consisting of tamoxifen and endoxifen a) 20 mg TAM + 0 mg END (for CYP2D6 EMs and UMs)
b) 20 mg TAM + 1 mg END (for CYP2D6 IMs)
c) 20 mg TAM + 3 mg END (for CYP2D6 PMs)

| | |
|---|---|
| ▨ | Tamoxifen (TAM) |
| ■ | Endoxifen (END) |

Figure 8

GENOTYPE- OR PHENOTYPE-BASED DRUG FORMULATION

This application is a 371 of International Patent Application No. PCT/EP2013/060824, filed May 27, 2013, which claims foreign priority benefit under 35 U.S.C. § 119 of European Patent Application No. 12170401.9, filed Jun. 1, 2012, the disclosures of which patent applications are incorporated herein by reference.

The invention relates to a combination of two or more pharmaceutically active substances, of which at least one is a metabolic product ("metabolite") of the other ("parent substance"), in particular the dosages thereof are selected such that genotypically or phenotypically (definition of genotype http://de.wikipedia.org/wiki/Genotyp, definition of phenotype: http://de.wikipedia.org/wiki/Ph%C3%A4notyp) related variability in the conversion of the parent substance to the metabolite(s) in particular individuals is compensated for.

The invention further relates to a combination of two or more pharmaceutically active substances, of which at least one is a metabolic product of the other, and the dosages thereof are selected such that genotypically or phenotypically related variability in transporters, receptors or other proteins involved in pharmacokinetic or pharmacodynamic processes of the parent substance and of the metabolite(s) in particular individuals is compensated for.

The principle according to the invention will be illustrated using the example of the combination of the breast cancer medicament tamoxifen and its active metabolite endoxifen.

In pharmacotherapy, there are numerous examples of pharmaceuticals, the pharmacological action of which arises from the interplay of the administered parent substance with metabolites which develop in the body of the patient. Such so-called active metabolites are generally formed via enzymatically catalysed processes, which can take place in, for example, the liver, the kidneys, the intestine or any other organ of the body. The activity of these enzymatic processes can widely differ in different individuals. The reasons for enzyme activities differing from individual to individual are diverse in nature. Firstly, there are individual variations in the quantity of the expressed enzyme variants which can be brought about by, for example, enzyme inhibitors or inducers or else genetic causes. Secondly, there are individual variations in the activity of the expressed enzyme variants which can occur owing to, for example, enzyme inhibitors or inducers or else genetic causes. Many active pharmaceutical ingredients are known cytochrome P450 enzyme inhibitors, for example:

2-(4-chlorophenoxy)ethanol, acarbose, acebutolol, acenocoumarol, acetazolamide, adefovir, ademetionine, ajmaline, albendazole, alitretinoin, allopurinol, alosetron, ambroxol, amphetamine, amilori de, aminoglutethimide, aminophenazone, amiodarone, amitriptyline, amlodipine, amodiaquine, amprenavir, anastrozole, androstandolone, aprepitant, aripiprazole, arsenic trioxide, artemisinin, artesunate, astemizole, atazanavir, atomoxetine, atorvastatin, atovaquone, atropine, azapropazone, azelastine, azithromycin, barnidipine, benazepril, benidipine, benzbromarone, benzethonium, benzocaine, bergapten, betamethasone, betaxolol, bezafibrate, bicalutamide, bifonazole, biperiden, bortezomib, bromazepam, bromocriptine, brompheniramine, budipine, buprenorphine, buprorion, calcitriol, candesartan, capecitabine, carbamazepine, carbinoxamine, carteolol, caspofungin, celecoxib, cerivastatin, quinidine, quinine, chloramphenicol, chlormadinone, chloroquine, chlorphenamine, chlorpromazine, chlorzoxazone, ciclosporin, cimetidine, ciprofibrate, ciprofloxacin, cisapride, cisplatin, citalopram, clarithromycin, clemastine, clevidipine, clindamycin, clobetasol, clofazimine, clofenotane, clofibrate, clomethiazole, clomifene, clomipramine, clonazepam, clopidogrel, clotiazepam, clotrimazole, clozapine, cocaine, codeine, caffeine, colchicine, colecalciferol, cyclizine, cylcophosphamide, cyproterone, dacarbazine, dactinomycin, dalfopristine, danazol, dantrolene, daunorubicin, deferoxamine, delavirdine, desipramine, desloratadine, desvenlafaxine, dexamethasone, dexamfetamine, dexfenfluramine, dexibuprofen, dextrometorphan, dextropropoxyphene, diazepam, diclofenac, dicoumarol, dihydralazine, dihydroergotamine, diiodohydroxypropane, diltiazem, dimethyl sulphoxide, dimetotiazine, diosmectite, diosmin, diphenhydramine, disulfiram, docetaxel, dolasetron, dopamine, doxepin, doxorubicin, doxycycline, ebastine, econazole, efavirenz, emetine, enoxacin, enoxolone, enprostil, entacapone, epinastine, epinephrine, eplerenone, eprosartan, ergometrine, ergotamine, erythromycin, escitalopram, estriol, etanautine, ethanol, ethinylestradiol, ethotoin, etodolac, etomidate, etoposide, etoricoxib, etretinate, exemestane, ezetimibe, felbamate, felodipine, fenfluramine, fenofibrate, fentanyl, fexofenadine, flecainide, flumequine, fluorouracil, fluoxetine, fluphenazine, flurazepam, flurbiprofen, flurithromycin, flutamide, fluvastatin, fluvoxamine, fomepizole, formestane, fosamprenavir, fosphenytoin, gefitinib, gemfibrozil, glibenclamide, gliclazide, glucose, glutethimide, granisetron, g-strophanthin, halofantrine, haloperidol, histamine, hydralazine, hydrocortisone, hydroxycarbamide, hydroxychloroquine, hydroxyzine, ibuprofen, idarubicin, ifosfamide, imatinib, imipramine, indinavir, indometacin, insulin, ipriflavone, irbesartan, irinotecan, isoconazole, isoflurane, isoniazid, isoprenaline, isopropanol, isosorbide dinitrate, isradipine, itraconazole, josamycin, ketoconazole, ketoprofen, labetalol, lafutidine, lansoprazole, leflunomide, lentinan, lercarnidipine, letrozole, levofloxacin, levomepromazine, levonorgestrel, lidocaine, lomefloxacin, lomustine, loperamide, lopinavir, loratadine, lornoxicam, losartan, lovastatin, manidipine, masoprocol, meclozine, medazepam, medroxyprogesterone, medrysone, mefenamic acid, mefloquine, meglutol, melatonin, meloxicam, melperone, memantine, menadione, mephenytoin, mequitazine, mesuximide, metamfetamine, metformin, methadone, methazolamide, methoxsalen, methylphenidate, methylphenobarbital, methylprednisolone, metoclopramide, metoprolol, metronidazole, metyrapone, mexiletine, mianserin, mibefradil, miconazole, midazolam, midecamycin, midodrine, mifepristone, minoxidil, miocamycin, mirtazapine, mitoxantrone, mizolastine, moclobemide, modafinil, mometasone, montelukast, moracizine, nefazodone, nelfinavir, neostigmine, nevirapine, nicardipine, niclosamide, nicotinamide, nifedipine, nicotine, nicotic acid, nilutamide, nilvadipine, nimesulide, nisoldipine, nitrendipine, nitroprusside, norepinephrine, norfloxacin, nortriptyline, noscapine, octopamine, ofloxacin, olanzapine, oleandomycin, omeprazole, ondansetron, orphenadrine, oxamniquine, oxatomide, oxcarbazepine, oxprenolol, oxybutynin, oxycodone, paclitaxel, pancreozymin (cholecystokinin), pantoprazole, paracetamol, parecoxib, pargyline, paroxetine, pazopanib, pefloxacin, pentoxyverin, perazine, pergolide, perhexiline, perphenazine, phenazone, phenelzine, phenobarbital, phensuximide, phentermine, phenylbutazone, phenylpropanolamine, phenytoin, physostigmine, pilocarpine, pimozide, pindolol, pioglitazone, piroxicam, pranlukast, prasterone, pravastatin, praziquantel, prednisolone, prednisone, primaquine, pristinamycin, probenecid, progesterone, proguanil, promethazine, propafenone, propanol, propiverine, propofol, propranolol, pyrimethamine, quassia, mercury, quetiapine, quinidine, quinine, quinupristin, rabeprazole, raloxifene, ranitidine, reboxetine, retinol, rifampicin, risperidone, ritonavir, rivastigmine, rofecoxib, rokitamycin, ropinirole, rosiglitazone, rosuvastatin, roxithromycin, rutoside, salbutamol, salicylamide, salmeterol, saquinavir, selegiline, seratrodast, sertaconazole, sertraline, sildenafil, silymarin, simvastatin, sirolimus, somatostatin, sorbitol, sparteine, spironolactone, nitrogen monoxide, sulconazole, sulfadiazine, sulfadimethoxine, sulfadimidine, sulfafurazole, sulfamethizole, sulfamethoxazole, sulfamoxole, sulfanilamide, sulfaphenazole, sulfapyridine, sulfinpyrazone, sulindac, sulpiride, suprofen, tacrolimus, tamoxifen, tegaserod, telithromycin, telmisartan, temafloxacin, teniposide, tenofovir, terbinafine, terconazole, terfenadine, teriparatide, testosterone, tetracycline, theophylline, thiamazole, thiopental, thioridazine, thiosulphate, thiotepa, tiabendazole, tibolone, ticlopidine, timolol, tinidazole, tioconazole, tiopronin, tiotixen, tocainide, tocopherol, tofisopam, tolbutamide, tolcapone, topiramate, topotecan, torasemide, tramadol, tranylcypromine, trastuzumab, treosulfan, tretinoin, triamterene, triazolam, trichloroethylene, triclosan, trimethoprim, tripelennamine, triprolidine, troglitazone, troleandomycin, tropisetron, trospium, ursodeoxycholic acid, valdecoxib, valproic acid, valsartan, venlafaxine, verapamil, vinblastine, vincristine, vinorelbine, virginiamycin, voriconazole, vorozole, warfarin, yohimbine, zafirlukast, ziprasidone, zolpidem, zonisamide.

Particular emphasis is given here to: fluvoxamine, ciprofloxacin, gemfibrozil, bupropion, cinacalcet, fluoxetine, paroxetine, quinidine, indinavir, nelfinavir, ritonavir, clarithromycin, itraconazole, ketoconazole, nefazodone, saquinavir, telithromycin, trimethoprim, amiodarone, duloxetine, sertraline, terbinafine, aprepitant, erythromycin, verapamil, diltiazem, cimetidine, amiodarone [http://medicine.iupui.edu/clinpharm/ddis/table.aspx as of 9 May 5, 2012].

Known inhibitors of phase 2 enzymes are, inter alia:
acarbose, acetylcholine, acetylsalicylic acid, amitriptyline, apomorphine, artemisinin, ascorbic acid, bendroflumethiazide, bergapten, bromocriptine, carbachol, carbamazepine, carmustine, celecoxib, chenodeoxycholic acid, quinine, chlorhexidine, chloroquine, cimetidine, clomipramine, clonidine, cocaine, cortisone, dactinomycin, desipramine, diazepam, dicoumarol, dicycloverine, diosmin, disulfiram, doxepin, enoxolone, entacapone, estradiol, etacrynic acid, fluconazole, fluphenazine, folic acid, haloperidol, hematin, hydrocortisone, hymecromone, ibuprofen, imipramine, indometacin, iproniazid, ketoprofen, lidocaine, lopinavir, medroxyprogesterone, melatonin, mepacrine, mere aptamine, mersalyl, mesalazine, methyldopa, moclobemide, naproxen, sodium citrate, sodium salicylate, niflumic acid, nicotine, olsalazine, oxedrine, paclitaxel, pargyline, phenylbutazone, physostigmine, pipamperone, polihexanide, primaquine, probenecid, progesterone, propylthiouracil, pyridoxal, pyridoxine, pyrimethamine, ranitidine, ritonavir, salicylamide, salicylic acid, saquinavir, silymarin, sulphobromophthalein, sulindac, tacrine, tamoxifen, tetracycline, thiomersal, tolcapone, triclosan, tubocurarine, vecuronium, warfarin, hydrogen peroxide.

Examples of known cytochrome P450 enzyme inducers are:
2-(4-chlorophenoxy)ethanol, acarbose, acetylsalicylic acid, acriflavinium chloride, albendazole, aldosterone, alum, aminoglutetimide, aminosalicylic acid, amobarbital, angiotensinamide, aprepitant, aprobarbital, aripiprazole, artemisinin, ascorbic acid, azatidine, beclometasone, benoxaprofen, beta-carotene, betamethasone, bexarotene, bezafibrate, biotin, bosentan, bucladesine, buserelin, captopril, carbamazepine, carbamide, carboplatin, quinidine, quinine, chlordiazepoxide, chlorothiazide, chlorpromazine, ciclosporin, ciprofibrate, ciprofloxacin, cisplatin, calcitriol, clarithromycin, clofenotane, clofibrate, clomifen, clonazepam, clonidine, clotrimazole, clozapine, colchicine, colestyramine, corticotropin, cyclobarbital, cyclophosphamide, dapsone, daunorubicin, dexamethasone, dextropropoxyphene, diazepam, dibutyl phthalate, diclofenamide, dicloxacillin, dicycloverine, diethyl ether, diethylstilbestrol, diiodohydroxypropane, dinoprostone, diosmectite, diosmin, docetaxel, doxorubicin, doxylamine, efavirenz, eletriptan, enoxacin, ergocalciferol, erythromycin, estriol, ethanol, ethinylestradiol, etoposide, fenbendazole, felbamate, fluconazole, flucloxacillin, flufenamic acid, fluorescein, fluvastatin, gemfibrozil, glucose, glutathione, glycerol, glycyrrhizic acid, granisetron, griseofulvin, guanethidine, haloperidol, histamine, hydrocortisone, hydroxycarbamide, ifosfamide, insulin, ipriflavone, isoflurane, isoniazid, isoprenaline, isopropanol, itraconazole, ketoconazole, cocaine, lansoprazole, lindane, loratadine, lovastatin, lynestrenol, mebendazole, mecamylamine, medroxyprogesterone, metamizole, methadone, metharbital, methohexital, methylprednisolone, methyltestosterone, metoclopramide, metyrapone, mifepristone, mirtazapine, mitobronitol, mitomycin, mitotane, moclobemide, modafinil, sodium chloride, sodium salicylate, nelfinavir, nevirapine, nicardipine, nicotinamide, nifedipine, nicotine, nitrazepam, norethisterone, omeprazole, ondansetron, oxcarbazepine, oxiconazole, oxolamine, oxomemazine, paclitaxel, pantoprazole, paracetamol, permethrin, pethidine, phenobarbital, phenoxymethylpenicillin, phentermine, phenylbutazone, phenylephrine, phenytoin, pindolol, pioglitazone, pipamperone, pleconaril, prednisolone, prednisone, primaquine, primidone, pristinamycin, probenecid, progesterone, propylthiouracil, pyridostigmine, pyridoxine, mercury, quinine, rabeprazole, reboxetine, reserpine, retinol, rifabutin, rifampicin, rifapentine, rifaximin, ritonavir, rofecoxib, salicylic acid, secobarbital, seratrodast, silymarin, spironolactone, streptozocin, sulfadimidine, sulfinpyrazone, tamoxifen, temozolomide, terbinafine, terfenadine, testosterone, tetrabenazine, tetramethrin, thalidomide, thiamine, thiram, tiabendazole, tienilic acid, tocopherol, topiramate, topotecan, tretinoin, triamcinolone acetonide, triamcinolone, troglitazone, tryptophan, ursodeoxycholic acid, valproic acid, verapamil, vinblastine, virginiamycin, voglibose.

Particular emphasis is given here to: modafinil, nafcillin, omeprazole, phenobarbital, phenytoin, rifampin, secobarbital, carbamazepine, norethindrone, prednisone, rifampicin, dexamethasone, isoniazid, efavirenz, nevirapine, barbiturates, glucocorticoids, oxcarbazepine, pioglitazone, rifabutin, troglitazone [http://medicine.iupui.edu/clinpharm/ddis/table.aspx as of 9 May 2012].

The known inducers of phase 2 enzymes include, inter alia:

acetylcholine, acetylsalicylic acid, adenosine, amfetamine, aminophylline, androstanolone, angiotensinamide, argatroban, ascorbic acid, benfluorex, beta-carotene, betamethasone, bucladesine, calcitriol, carbamazepine, chlorambucil, chlorphenamine, cisapride, cisplatin, clofibrate, clozapine, cocaine, corticotropin, desipramine, dexamethasone, dexamfetamine, diazepam, diclofenac, diethylcarbamazine, diethyl ether, dinoprostone, disulfiram, doxorubicin, entacapone, epinephrine, esketamine, estradiol, estriol, ethanol, flunarizine, fluoxetine, gabapentin, glyceryl trinitrate, glycine, g-strophantin, hydralazine, hydrocortisone, hymecromone, ibuprofen, imipramine, indometacin, insulin, isoprenaline, ketamine, lamotrigine, levetiracetam, levodopa, lindane, melatonin, melphalan, mequinol, metamizole, methionine, methotrexate, metoclopramide, nabumetone, nandrolone, norepinephrine, olanzapine, paracetamol, pargyline, phenobarbital, phenytoin, pipamperone, progesterone, promegestone, propylthiouracil, retinol, rofecoxib, spironolactone, nitrogen monoxide, sulindac, sultiame, tamoxifen, testosterone, theophylline, tiadenol, tibolone, tioguanine, triamcinolone, trimethoprim, troglitazone, valproic acid, verapamil, warfarin, hydrogen peroxide.

[http://bioinformatics.charite.de/supercyp as of 24 Apr. 2012]. Besides active pharmaceutical ingredients, dietary components may also have inhibitory and/or inducing effects on enzymes, transporters, receptors or other proteins.

Known examples thereof are, inter alia: broccoli, grilled meat, St John's wort, tobacco smoke, cheese, red wine, grapefruit juice, folic acid, vitamin K, vitamin E, vitamin B6 and St John's wort [Gröber, U. (2009) "Interaktionen Arzneimittel and Mikronährstoffe für die Kitteltasche [Interactions: Pharmaceuticals and Micronutrients (Pocket Guide)]" Wissenschaftliche Verlagsgesellschaft mbH Stuttgart; Wentworth, J. M., M. Agostini, et al. (2000). "St John's wort, a herbal antidepressant, activates the steroid X receptor." J Endocrinol 166(3): R11-16., http://medicine.iupui.edu/clinpharm/ddis/table.aspx as of 9 May 2012]. Similar to the inducing effect of grilled meat on cytochrome P450 1A1 (CYP1A1), the enzyme can also be induced by polycyclic aromatics, which are present in cigarette smoke. For instance, it is described in the literature that the activity of CYP1A1 in the lungs, liver and intestine of smokers is increased in proportion to their cigarette consumption [Czekaj, P., A. Wiaderkiewicz, et al. (2005). "Tobacco smoke-dependent changes in cytochrome P450 1A1, 1A2, and 2E1 protein expressions in fetuses, newborns, pregnant rats, and human placenta." Arch Toxicol 79(1): 13-24.; Fontana, R. J., K. S. Lown, et al. (1999). "Effects of a chargrilled meat diet on expression of CYP3A, CYP1A, and P-glycoprotein levels in healthy volunteers." Gastroenterology 117(1): 89-98.; Kim, J. H., M. E. Sherman, et al. (2004). "Expression of cytochromes P450 1A1 and 1B1 in human lung from smokers, non-smokers, and ex-smokers." Toxicol Appl Pharmacol 199(3): 210-219., Pelkonen, O., M. Pasanen, et al. (1986). "The effect of cigarette smoking on 7-ethoxyresorufin O-deethylase and other monooxygenase activities in human liver: analyses with monoclonal antibodies." Br J Clin Pharmacol 22(2): 125-134.; Zevin, S. and N. L. Benowitz (1999). "Drug interactions with tobacco smoking. An update." Clin Pharmacokinet 36(6): 425-438.].

Furthermore, the pharmacological action of the parent substance and its metabolite(s) may also be dependent on the quantity or the activity of expressed protein variants, receptor variants or transporter variants, which may likewise greatly differ from individual to individual or within an individual owing to inhibition or induction or genetic causes.

Examples of transporter inducers are: dexamethasone, doxorubicin, flavonoids, St John's wort, phenobarbital, phenytoin, rifampicin, vinblastine.

Examples of transporter inhibitors are:

rifampicin, cyclosporin A, gemfibrozil, lopinavir, ritonavir, clarithromycin, furosemide, indometacin, probenecid, naproxen, ibuprofen, piroxicam, acetylsalicylic acid, paracetamol, phenacetin, ketoprofen, enalapril, bumetanide, cefoperazone, azathioprine, methotrexate, valproate, flufenamate, phenylbutazone, levofloxacin, dexamethasone, cytarabine, ampicillin, amoxicillin, ciclacillin, cephalexin, cefadroxil, cephradine, cefdinir, ceftibuten, cefixime, captopril, amiodarone, quinidine, lidocaine, itraconazole, ketoconazole, diltiazem, felodipine, nicardipine, nifedipine, nitrendipine, verapamil, indinavir, nelfinavir, saquinavir, ethinylestradiol, norgestrel, progesterone, testosterone, tacrolimus, erythromycin, mifepristone, paroxetine, talinolol, tamoxifen, terfenadine, trifluoperazine, vincristine.

[Shitara, Y. (2011). "Clinical importance of OATP1B1 and OATP1B3 in drug-drug interactions." Drug Metab Pharmacokinet 26(3): 220-227.; Van Aubel, R. A., R. Masereeuw, et al. (2000). "Molecular pharmacology of renal organic anion transporters." Am J Physiol Renal Physiol 279(2): F216-232.; http://www.pharmazeutische-zeitung.de/index.php?id=2381].

Of particular importance to pharmacotherapy are those differences in protein activity which have a genetic cause. As a result of sequence variations (http://de.wikipedia.org/wiki/Polymorphismus) in the alleles and/or as a result of a varying number of alleles present, it is possible for different variants and/or quantities of a protein to be expressed. Both, the expressed variant and the expressed quantity of a protein, can have a strong influence on the activity of the protein variant.

In the literature, a well studied example of a polymorphic protein is cytochrome P450 2D6 (CYP2D6), an enzyme for which it is known that there is a multiplicity of different gene variants which can be classified into four different phenotypes. The customary designations for this purpose are: PM="poor metabolizer", IM="intermediate metabolizer", EM="extensive metabolizer" and UM="ultrarapid metabolizer" [Zanger, U. M., J. Fischer, et al. (2001). "Comprehensive analysis of the genetic factors determining expression and function of hepatic CYP2D6." Pharmacogenetics 11(7): 573-585].

Besides CYP2D6, there are numerous other polymorphic enzymes from the class of cytochrome P450 (CYP) isoenzymes:

CYP1A1, CYP1A2, CYP1B1, CYP2A6, CYP2A13, CYP2B6, CYP2C8, CYP2C9, CYP2C11, CYP2C18, CYP2C19, CYP2D6, CYP2E1, CYP2F1, CYP2J2, CYP2S1, CYP2W1, CYP3A4, CYP3A5, CYP3A7, CYP3A43, CYP4A11, CYP4B1, CYP4F2, CYP4F22, CYP7A1, CYP4B1, CYP7B1, CYP8A1, CYP8B1, CYP11A, CYP11B1, CYP11B2, CYP17A, CYP19A,

CYP21A, CYP24A, CYP26A1, CYP26B, CYP27A. CYP27B, CYP46A, CYP51A.

Particular emphasis is given here to: CYP1A2, CYP2B6, CYP2C8, CYP2C9, CYP2C19, CYP2D6, CYP2E1, CYP3A4, CYP3A5, CYP3A7 [http://bioinformatics.charite.de/supercyp as of 24 Apr. 2012; Tamaki, Y., T. Arai, et al. (2011). "Association between cancer risk and drug-metabolizing enzyme gene (CYP2A6, CYP2A13, CYP4B1, SULT1A1, GSTM1, and GSTT1) polymorphisms in cases of lung cancer in Japan." Drug Metab Pharmacokinet 26(5): 516-522.].

There are similarly numerous polymorphic phase 2 enzymes or other enzymes in metabolism, for example:

N-acetyltransferase 2 (NAT2), thiopurine S-methyltransferase (TPMT), uridine 5'-diphospho-glucuronosyltransferase (UGT) 1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B15, UGT2B17, sulfotransferase (SULT) 1A1, SULT1A2, SULT1A3, SULT1E1, SULT2A1, SULT2B1, SULT4A1, glutathione S-transferase (GST) A1, GSTA2, GSTA3, GSTA4, GSTA5, GSTM1, GSTM2, GSTM3, GSTM4, GSTM5, GSTP1, GSTT1, GSTT2, GSTO1, GSTO2, catechol-o-methyltransferase (COMT), flavin-dependent monooxygenase 3 (FMO), dihydropyrimidine dehydrogenase (DPD), methylenetetrahydrofolate reductase (MTHFR).

Particular emphasis is given here to: NAT2, TPMT, UGT1A1, UGT1A4, UGT2B7, UGT2B15, SULT1A1, SULT1A2, SULT2A1, GSTM1, GSTP1, GSTT1, COMT, DPD, MTHFR [Hickman, D. and E. Sim (1991). "N-acetyltransferase polymorphism. Comparison of phenotype and genotype in humans." Biochem Pharmacol 42(5): 1007-1014.; Yates, C. R., E. Y. Krynetski, et al. (1997). "Molecular diagnosis of thiopurine S-methyltransferase deficiency: genetic basis for azathioprine and mercaptopurine intolerance." Ann Intern Med 126(8): 608-614.; Bernard, O., J. Tojcic, et al. (2006). "Influence of nonsynonymous polymorphisms of UGT1A8 and UGT2B7 metabolizing enzymes on the formation of phenolic and acyl glucuronides of mycophenolic acid." Drug Metab Dispos 34(9): 1539-1545.; Bushey, R. T., G. Chen, et al. (2011). "Characterization of UDP-glucuronosyltransferase 2A1 (UGT2A1) variants and their potential role in tobacco carcinogenesis." Pharmacogenet Genomics 21(2): 55-65.; Carlini, L. E., N. J. Meropol, et al. (2005). "UGT1A7 and UGT1A9 polymorphisms predict response and toxicity in colorectal cancer patients treated with capecitabine/irinotecan." Clin Cancer Res 11(3): 1226-1236.; Chen, G., A. S. Blevins-Primeau, et al. (2007). "Glucuronidation of nicotine and cotinine by UGT2B10: loss of function by the UGT2B10 Codon 67 (Asp>Tyr) polymorphism." Cancer Res 67(19): 9024-9029.; Chen, G., R. W. Dellinger, et al. (2008). "Identification of a prevalent functional missense polymorphism in the UGT2B10 gene and its association with UGT2B10 inactivation against tobacco-specific nitrosamines" Pharmacogenet Genomics 18(3): 181-191.; Chen, Y., S. Chen, et al. (2006). "Genetic variants of human UGT1A3: functional characterization and frequency distribution in a Chinese Han population." Drug Metab Dispos 34(9): 1462-1467.; Dellinger, R. W., J. L. Fang, et al. (2006). "Importance of UDP-glucuronosyltransferase 1A10 (UGT1A10) in the detoxification of polycyclic aromatic hydrocarbons: decreased glucuronidative activity of the UGT1A10139Lys isoform." Drug Metab Dispos 34(6): 943-949.; Guo, Y., C. Hu, et al. (2012). "Effects of UGT1A6, UGT2B7, and CYP2C9 genotypes on plasma concentrations of valproic acid in Chinese children with epilepsy." Drug Metab Pharmacokinet.; He, X., L. M. Hesse, et al. (2009). "Evidence for oxazepam as an in vivo probe of UGT2B15: oxazepam clearance is reduced by UGT2B15 D85Y polymorphism but unaffected by UGT2B17 deletion." Br J Clin Pharmacol 68(5): 721-730.; Park, W. B., P. G. Choe, et al. (2010). "Genetic factors influencing severe atazanavir-associated hyperbilirubinemia in a population with low UDP-glucuronosyltransferase 1A1*28 allele frequency." Clin Infect Dis 51(1): 101-106.; Parmar, S., J. C. Stingl, et al. (2011). "Impact of UGT2B7 His268Tyr polymorphism on the outcome of adjuvant epirubicin treatment in breast cancer." Breast Cancer Res 13(3): R57.; Saeki, M., Y. Saito, et al. (2004). "Single nucleotide polymorphisms and haplotype frequencies of UGT2B4 and UGT2B7 in a Japanese population." Drug Metab Dispos 32(9): 1048-1054.; Sneitz, N., M. H. Court, et al. (2009). "Human UDP-glucuronosyltransferase UGT2A2: cDNA construction, expression, and functional characterization in comparison with UGT2A1 and UGT2A3." Pharmacogenet Genomics.; Sun, D., G. Chen, et al. (2006). "Characterization of tamoxifen and 4-hydroxytamoxifen glucuronidation by human UGT1A4 variants." Breast Cancer Res 8(4): R50.; Swanson, C., D. Mellstrom, et al. (2007). "The uridine diphosphate glucuronosyltransferase 2B15 D85Y and 2B17 deletion polymorphisms predict the glucuronidation pattern of androgens and fat mass in men." J Clin Endocrinol Metab 92(12): 4878-4882.; Yang, J., L. Cai, et al. (2012). "Genetic Variations and Haplotype Diversity of the UGT1 Gene Cluster in the Chinese Population." PLoS One 7(4): e33988.; Arslan, S. (2010). "Genetic polymorphisms of sulfotransferases (SULT1A1 and SULT1A2) in a Turkish population." Biochem Genet 48(11-12): 987-994.; Hirata, H., Y. Hinoda, et al. (2008). "CYP1A1, SULT1A1, and SULT1E1 polymorphisms are risk factors for endometrial cancer susceptibility." Cancer 112(9): 1964-1973.; Ji, Y., I. Moon, et al. (2007). "Human hydroxysteroid sulfotransferase SULT2B1 pharmacogenomics: gene sequence variation and functional genomics." J Pharmacol Exp Ther 322(2): 529-540.; Ramsey, T. L., H. Y. Meltzer, et al. (2011). "Evidence for a SULT4A1 haplotype correlating with baseline psychopathology and atypical antipsychotic response." Pharmacogenomics 12(4): 471-480.; Tamaki, Y., T. Arai, et al. (2011). "Association between cancer risk and drug-metabolizing enzyme gene (CYP2A6, CYP2A13, CYP4B1, SULT1A1, GSTM1, and GSTT1) polymorphisms in cases of lung cancer in Japan." Drug Metab Pharmacokinet 26(5): 516-522.; Thomae, B. A., B. W. Eckloff, et al. (2002). "Human sulfotransferase SULT2A1 pharmacogenetics: genotype-to-phenotype studies." Pharmacogenomics J 2(1): 48-56.; Thomae, B. A., 0. F. Rifki, et al. (2003). "Human catecholamine sulfotransferase (SULT1A3) pharmacogenetics: functional genetic polymorphism." J Neurochem 87(4): 809-819.; Breton, C. V., H. Vora, et al. (2009). "Variation in the GST mu locus and tobacco smoke exposure as determinants of childhood lung function." Am J Respir Crit Care Med 179(7): 601-607.; Chen, Y. L., H. S. Tseng, et al. (2010). "Glutathione S-Transferase P1 (GSTP1) gene polymorphism increases age-related susceptibility to hepatocellular carcinoma." BMC Med Genet 11: 46.; Coles, B. F., F. Morel, et al. (2001). "Effect of polymorphism in the human glutathione S-transferase A1 promoter on hepatic GSTA1 and GSTA2 expression." Pharmacogenetics 11(8): 663-669.; Moyer, A. M., Z. Sun, et al. (2010). "Glutathione pathway genetic polymorphisms and lung cancer survival after platinum-based chemotherapy." Cancer Epidemiol Biomarkers Prev 19(3): 811-821.; Tetlow, N., M. Coggan, et al. (2004). "Functional polymorphism of human glutathione transferase A3: effects on xenobiotic metabolism and steroid biosynthesis." Pharmacogenetics 14(10): 657-663.; Tran, A., F. Bournerias, et al. (2008). "Serious haematological toxicity of cyclophosphamide in relation to CYP2B6, GSTA1 and GSTP1 polymorphisms." Br J Clin Pharmacol 65(2): 279-280.; White, D. L., D. Li, et al. (2008). "Genetic variants of glutathione S-transferase as possible risk factors for hepatocellular carcinoma: a HuGE systematic review and meta-analysis." Am J Epidemiol 167(4): 377-389.; Zhao, Y., M. Marotta, et al. (2009). "Linkage disequilibrium between two high-frequency deletion polymorphisms: implications for association studies involving the glutathione-S transferase (GST) genes." PLoS Genet 5(5): e1000472.; Motika, M. S., J. Zhang, et al. (2009). "Novel variants of the human flavin-containing monooxygenase 3 (FMO3) gene associated with trimethylaminuria." Mol Genet Metab 97(2): 128-135.; Voisey, J., C. D. Swagell, et al. (2011). "A novel SNP in COMT is associated with alcohol dependence but not opiate or nicotine dependence: a case control study." Behav Brain Funct 7: 51.; Fisher, M. C. and B. N. Cronstein (2009). "Meta-analysis of methylenetetrahydrofolate reductase (MTHFR) polymorphisms affecting methotrexate toxicity." J Rheumatol 36(3): 539-545.; Zhang, X. P., Z. B. Bai, et al. (2012). "Polymorphisms of dihydropyrimidine dehydrogenase gene and clinical outcomes of gastric cancer patients treated with fluorouracil-based adjuvant chemotherapy in Chinese population." Chin Med J (Engl) 125(5): 741-746.].

There are also numerous examples of polymorphic transporters and/or receptors and/or other proteins.

Examples of polymorphic transporters are:
ABCA1, ABCA2, ABCA3, ABCA4, ABCA7, ABCA8, ABCA12, ABCA13, ABCB1, ABCB2, ABCB4, ABCB5, ABCB7, ABCB8, ABCB9, ABCB10, ABCB11, ABCC1, ABCC2, ABCC3, ABCC4, ABCC5, ABCC6, ABCC8, ABCC9, ABCC10, ABCC11, ABCD1, ABCD2, ABCD3, ABCD4, ABCe1, ABCF1, ABCG1, ABCG2, ABCG4, ABCG5, ABCG8, OAT1, OAT2, OAT3, OAT4, URAT5, OATP1A2, OATP1B1, OATP1B3, OATP1C1, OATP1B1, OCT1, OCT2, OCT3, OCTN1, OCTN2, SLC22A16

[Akiyama, Y., K. I. Fujita, et al. (2011). "Association of ABCC2 genotype with efficacy of first-line FOLFIRI in Japanese patients with advanced colorectal cancer." Drug Metab Pharmacokinet.; Fukao, M., K. Ishida, et al. (2011). "Effect of genetic polymorphisms of SLC28A1, ABCG2, and ABCC4 on bioavailability of mizoribine in healthy Japanese males." Drug Metab Pharmacokinet 26(5): 538-543.; Garcia-Donas, J., E. Esteban, et al. (2011). "Single nucleotide polymorphism associations with response and toxic effects in patients with advanced renal-cell carcinoma treated with first-line sunitinib: a multicentre, observational, prospective study." Lancet Oncol 12(12): 1143-1150.; Hollingworth, P., D. Harold, et al. (2011). "Common variants at ABCA7, MS4A6A/MS4A4E, EPHA1, CD33 and CD2AP are associated with Alzheimer's disease." Nat Genet 43(5): 429-435.; Iida, A., S. Saito, et al. (2002). "Catalog of 605 single-nucleotide polymorphisms (SNPs) among 13 genes encoding human ATP-binding cassette transporters: ABCA4, ABCA7, ABCA8, ABCD1, ABCD3, ABCD4, ABCE1, ABCF1, ABCG1, ABCG2, ABCG4, ABCG5, and ABCG8." J Hum Genet 47(6): 285-310.; Karadeniz, M., M. Erdogan, et al. (2011). "Effect Of G2706A and G105 1A polymorphisms of the ABCA1 gene on the lipid, oxidative stress and homocystein levels in Turkish patients with polycystic ovary syndrome." Lipids Health Dis 10: 193.; Kelsell, D. P., E. E. Norgett, et al. (2005). "Mutations in ABCA12 underlie the severe congenital skin disease harlequin ichthyosis." Am J Hum Genet 76(5): 794-803.; Knight, H. M., B. S. Pickard, et al. (2009). "A cytogenetic abnormality and rare coding variants identify ABCA13 as a candidate gene in schizophrenia, bipolar disorder, and depression." Am J Hum Genet 85(6): 833-846.; Kwan, P., V. Wong, et al. (2011). "Gene-wide tagging study of the association between ABCC2, ABCC5 and ABCG2 genetic polymorphisms and multidrug resistance in epilepsy." Pharmacogenomics 12(3): 319-325.; Liptrott, N. J., S. Pushpakom, et al. (2012). "Association of ABCC10 polymorphisms with nevirapine plasma concentrations in the German Competence Network for HIV/AIDS." Pharmacogenet Genomics 22(1): 10-19.; Maia-Lopes, S., J. Aguirre-Lamban, et al. (2009). "ABCA4 mutations in Portuguese Stargardt patients: identification of new mutations and their phenotypic analysis." Mol Vis 15: 584-591.; Matsukawa, T., M. Asheuer, et al. (2011). "Identification of novel SNPs of ABCD1, ABCD2, ABCD3, and ABCD4 genes in patients with X-linked adrenoleukodystrophy (ALD) based on comprehensive resequencing and association studies with ALD phenotypes." Neurogenetics 12(1): 41-50.; Minster, R. L., S. T. DeKosky, et al. (2009). "No association of DAPK1 and ABCA2 SNPs on chromosome 9 with Alzheimer's disease." Neurobiol Aging 30(11): 1890-1891.; Moitra, K., M. Scally, et al. (2011). "Molecular evolutionary analysis of ABCB5: the ancestral gene is a full transporter with potentially deleterious single nucleotide polymorphisms." PLoS One 6(1): e16318.; Pietrzak-Nowacka, M., K. Safranow, et al. (2012). "Association of C49620T ABCC8 polymorphism with anthropometric and metabolic parameters in patients with autosomal dominant polycystic kidney disease: a preliminary study." Nefrologia 32(2): 153-159.; Saito, S., A. Iida, et al. (2002). "Identification of 779 genetic variations in eight genes encoding members of the ATP-binding cassette, subfamily C (ABCC/MRP/CFTR." J Hum Genet 47(4): 147-171.; Saito, S., A. Iida, et al. (2002). "Three hundred twenty-six genetic variations in genes encoding nine members of ATP-binding cassette, subfamily B (ABCB/MDR/TAP), in the Japanese population." J Hum Genet 47(1): 38-50.; Sasaki, T., T. Hirota, et al. (2011). "Systematic screening of human ABCC3 polymorphisms and their effects on MRP3 expression and function." Drug Metab Pharmacokinet 26(4): 374-386.; Schulz, V., D. Hendig, et al. (2005). "Analysis of sequence variations in the ABCC6 gene among patients with abdominal aortic aneurysm and pseudoxanthoma elasticum." J Vasc Res 42(5): 424-432.; Shulenin, S., L. M. Nogee, et al. (2004). "ABCA3 gene mutations in newborns with fatal surfactant deficiency." N Engl J Med 350(13): 1296-1303.; Toyoda, Y. and T. Ishikawa (2010). "Pharmacogenomics of human ABC transporter ABCC11 (MRP8): potential risk of breast cancer and chemotherapy failure." Anticancer Agents Med Chem 10(8): 617-624.; Wasmuth, H. E., A. Glantz, et al. (2007). "Intrahepatic cholestasis of pregnancy: the severe form is associated with common variants of the hepatobiliary phospholipid transporter ABCB4 gene." Gut 56(2): 265-270.; Yin, J. Y., Q. Huang, et al. (2009). "Characterization and analyses of multidrug resistance-associated protein 1 (MRP1/ABCC1) polymorphisms in Chinese population." Pharmacogenet Genomics 19(3): 206-216.; Yu, X., H. Xie, et al. (2011). "Association of MDR1 gene SNPs and haplotypes with the tacrolimus dose requirements in Han Chinese liver transplant recipients." PLoS One 6(11): e25933.; Lee, W., H. Glaeser, et al. (2005). "Polymorphisms in human organic anion-transporting polypeptide 1A2 (OATP1A2): implications for altered drug disposition and central nervous system drug entry." J Biol Chem 280(10): 9610-9617.; Mougey, E. B., H. Feng, et al. (2009). "Absorption of montelukast is transporter mediated: a common variant of OATP2B1 is associated with reduced plasma concentrations and poor response." Pharmacogenet Genomics 19(2): 129-138.; Trdan Lu 353 In, T., B. Stieger, et al. (2012). "Organic anion transporting polypeptides OATP1B1 and OATP1B3 and their genetic variants influence the pharmacokinetics and pharmacodynamics of raloxifene." J Transl Med 10(1): 76.; van der Deure, W. M., P. S. Hansen, et al. (2008). "Thyroid hormone transport and metabolism by organic anion transporter 1C1 and consequences of genetic variation." Endocrinology 149(10): 5307-5314.; Vormfelde, S. V., M. Schirmer, et al. (2006). "Torsemide renal clearance and genetic variation in luminal and basolateral organic anion transporters." Br J Clin Pharmacol 62(3): 323-335.; Xu, G., V. Bhatnagar, et al. (2005). "Analyses of coding region polymorphisms in apical and basolateral human organic anion transporter (OAT) genes [OAT1 (NKT), OAT2, OAT3, OAT4, URAT (RST)]." Kidney Int 68(4): 1491-1499.; Becker, M. L., L. E. Visser, et al. (2011). "OCT1 polymorphism is associated with response and survival time in anti-Parkinsonian drug users." Neurogenetics 12(1): 79-82., Lal, S., Z. W. Wong, et al. (2007). "Novel SLC22A16 polymorphisms and influence on doxorubicin pharmacokinetics in Asian breast cancer patients." Pharmacogenomics 8(6): 567-575., Park, T. J., J. H. Kim, et al. (2011). "Possible association of SLC22A2 polymorphisms with aspirin-intolerant asthma." Int Arch Allergy Immunol 155(4): 395-402., Sakata, T., N. Anzai, et al. (2010). "Functional analysis of human organic cation transporter OCT3 (SLC22A3) polymorphisms." J Pharmacol Sci 113(3): 263-266., Tahara, H., S. W. Yee, et al. (2009). "Functional genetic variation in the basal promoter of the organic cation/carnitine transporters OCTN1 (SLC22A4) and OCTN2 (SLC22A5)." J Pharmacol Exp Ther 329(1): 262-271.]

Particular emphasis is given here to: ABCB1 (p-glycoprotein), ABCC1 (MRP1), ABCG2 (BCRP), OATP1B1, OAT3, OCT1, OCT2, OCT3, SLC22A16.

In pharmacotherapy, such differences in enzyme activity or enzyme quantity may have a dramatic influence on the success of treatment, since they directly influence the pharmacokinetics—and here in particular the exposure—of the substances which are substrates for one or more polymorphic enzymes and of the metabolite(s) formed by the polymorphic enzyme. The same applies to such differences in protein activity or protein quantity, since receptors, transporters or other proteins may also directly influence the pharmacokinetics—and here in particular the exposure—of the substances which are substrates for one or more polymorphic proteins. In addition, a direct effect on the pharmacodynamics may also occur here if these proteins are involved in the mechanism of action.

There was therefore the need for improved pharmacotherapy in the use of active ingredients, the action of which is dependent on the quantity or the activity of expressed and/or inhibited/induced protein variants, enzyme variants, receptor variants or transporter variants, with said pharmacotherapy compensating for the aforementioned variations.

The present invention is based on a novel formulation concept, more particularly in the form of a fixed-dose combination (FDC), in which pre-known individual differences in the activity of a relevant protein are taken into consideration in the dosage of two or more pharmacologically active substances, of which one or more are metabolites of the other substance, in order to ensure optimal success of treatment. The novel formulation concept is based on compensation of the varying exposure to the parent substance and one or more active metabolites by a specific dosage of the combination of parent substance and one/more metabolites that is individually adapted to the genotype or phenotype. The pharmacokinetic goal is to establish a "bioequivalence"-like steady-state situation (i.e. following repeated intake), i.e. conformity of plasma concentration changes of the concerned substances within predefined limits (for this purpose, it is possible to use, for example, the criteria common in another context; see in this regard "Prior Art"), with respect to a reference population which has to be defined from the specific context.

BRIEF DESCRIPTION OF THE DRAWINGS

The invention will now be described in greater detail with reference to the drawings, wherein:

FIG. 8 shows genotype- or phenotype-based dosing of tamoxifen and endoxifen as a loose combination (A) or as an FDC (B).

To study the formulation concept according to the invention, pharmacotherapy with tamoxifen was chosen as an example, without restricting the concept to said example.

In the case of a CYP2D6 polymorphism, a population consisting of extensive metabolizers (EMs) would be an example of a meaningful reference population, since this phenotype represents the wild type and is the most widespread in many geographical regions [Sistonen, J., A. Sajantila, et al. (2007). "CYP2D6 worldwide genetic variation shows high frequency of altered activity variants and no continental structure." Pharmacogenet Genomics 17(2): 93-101.]. Using the example of a known cancer medicament, tamoxifen, the problem of genotype- or phenotype-dependent exposure of active metabolites shall be illustrated without being restrictive thereto.

Figure 1:
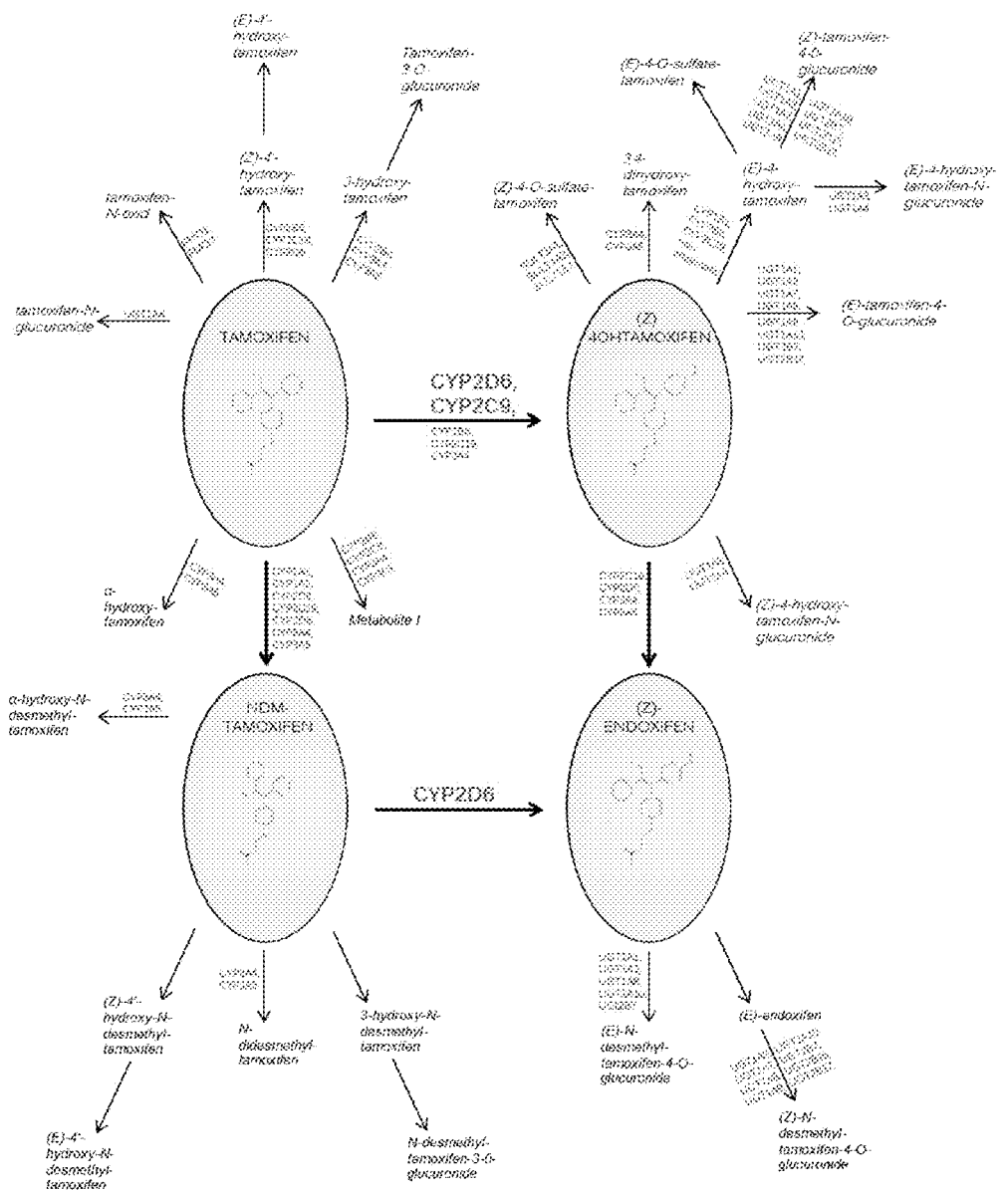
FIG. 1 shows an extract from the complex biotransformation scheme for tamoxifen in humans.

Tamoxifen is a well known pharmaceutical ingredient used for treating oestrogen receptor-positive (ER+) breast cancer. The parent substance is subject to a complex metabolization scheme, which is shown in FIG. 1. In the human body (among others), tamoxifen is converted into three active metabolites (N-desmethyltamoxifen, 4-hydroxytamoxifen, endoxifen). Among the active metabolites, endoxifen in particular, a secondary metabolite of tamoxifen, is of importance, since a large percentage of the formation of endoxifen is catalysed via the polymorphic CYP2D6. As a result, the endoxifen concentration in the blood of a breast cancer patient is dependent on the CYP2D6 genotype or phenotype thereof. In the case of a CYP2D6 PM, there is practically no CYP2D6 activity and the concentration of the active metabolite endoxifen is consequently very low [Murdter, T. E., W. Schroth, et al. (2011). "Activity levels of tamoxifen metabolites at the estrogen receptor and the impact of genetic polymorphisms of phase I and II enzymes on their concentration levels in plasma." Clin Pharmacol Ther 89(5): 708-717.; Jin, Y., Z. Desta, et al. (2005). "CYP2D6 Genotype, Antidepressant Use, and Tamoxifen Metabolism During Adjuvant Breast Cancer Treatment." Journal of the National Cancer Institute 97(1): 30-39.; Gjerde, J., M. Hauglid, et al. (2008). "Effects of CYP2D6 and SULT1A1 genotypes including SULT1A1 gene copy number on tamoxifen metabolism." Ann Oncol 19(1): 56-61.; Borges, S., Z. Desta, et al. (2006). "Quantitative effect of CYP2D6 genotype and inhibitors on tamoxifen metabolism: implication for optimization of breast cancer treatment." Clin Pharmacol Ther 80(1): 61-74.; Madlensky, L., L. Natarajan, et al. (2011). "Tamoxifen metabolite concentrations, CYP2D6 genotype, and breast cancer outcomes." Clin Pharmacol Ther 89(5): 718-725.; Lim, J. S., X. A. Chen, et al. (2011). "Impact of CYP2D6, CYP3A5, CYP2C9 and CYP2C19 polymorphisms on tamoxifen pharmacokinetics in Asian breast cancer patients." Br J Clin Pharmacol 71(5): 737-750.; Lim, H. S., H. Ju Lee, et al. (2007). "Clinical implications of CYP2D6 genotypes predictive of tamoxifen pharmacokinetics in metastatic breast cancer." J Clin Oncol 25(25): 3837-3845.; Kiyotani, K., T. Mushiroda, et al. (2010). "Significant effect of polymorphisms in CYP2D6 and ABCC2 on clinical outcomes of adjuvant tamoxifen therapy for breast cancer patients." J Clin Oncol 28(8): 1287-1293.; Irvin, W. J., Jr., C. M. Walko, et al. (2011). "Genotype-Guided Tamoxifen Dosing Increases Active Metabolite Exposure in Women With Reduced CYP2D6 Metabolism: A Multicenter Study." J Clin Oncol 29(24): 3232-3239.]. In the case of a CYP2D6 IM, the endoxifen concentration is likewise still distinctly below the level which can observed in the case of an EM or the (relatively rare in Europeans) UM phenotype. In this connection, a study also showed a distinct gene dosage effect between CYP2D6 EM, IM, and PM genotypes or phenotypes and their respective steady-state endoxifen concentrations [Jin, Y., Z. Desta, et al. (2005). "CYP2D6 Genotype, Antidepressant Use, and Tamoxifen Metabolism During Adjuvant Breast Cancer Treatment." Journal of the National Cancer Institute 97(1): 30-39]. The genotype- or phenotype-dependent exposures of endoxifen are shown by way of example in FIG. 2. Within a population of breast cancer patients, the exposure of endoxifen is thus dependent on the frequency distribution of the various CYP2D6 genotypes or phenotypes. This frequency distribution differs greatly between regions or ethnic groups [Bernard, S., K. A. Neville, et al. (2006). "Interethnic differences in genetic polymorphisms of CYP2D6 in the U.S. population: clinical implications." Oncologist 11(2): 126-135.; Bradford, L. D. (2002). "CYP2D6 allele frequency in European Caucasians, Asians, Africans and their descendants." Pharmacogenomics 3(2): 229-243.; Sachse, C., J. Brockmoller, et al. (1997). "Cytochrome P450 2D6 variants in a Caucasian population: allele frequencies and phenotypic consequences." Am J Hum Genet 60(2): 284-295.; Sistonen, J., A. Sajantila, et al. (2007). "CYP2D6 worldwide genetic variation shows high frequency of altered activity variants and no continental structure." Pharmacogenet Genomics 17(2): 93-101.]. In the case of Europeans, EM is the predominant genotype [Sistonen, J., A. Sajantila, et al. (2007). "CYP2D6 worldwide genetic variation shows high frequency of altered activity variants and no continental structure." Pharmacogenet Genomics 17(2): 93-101.].

Figure 3:
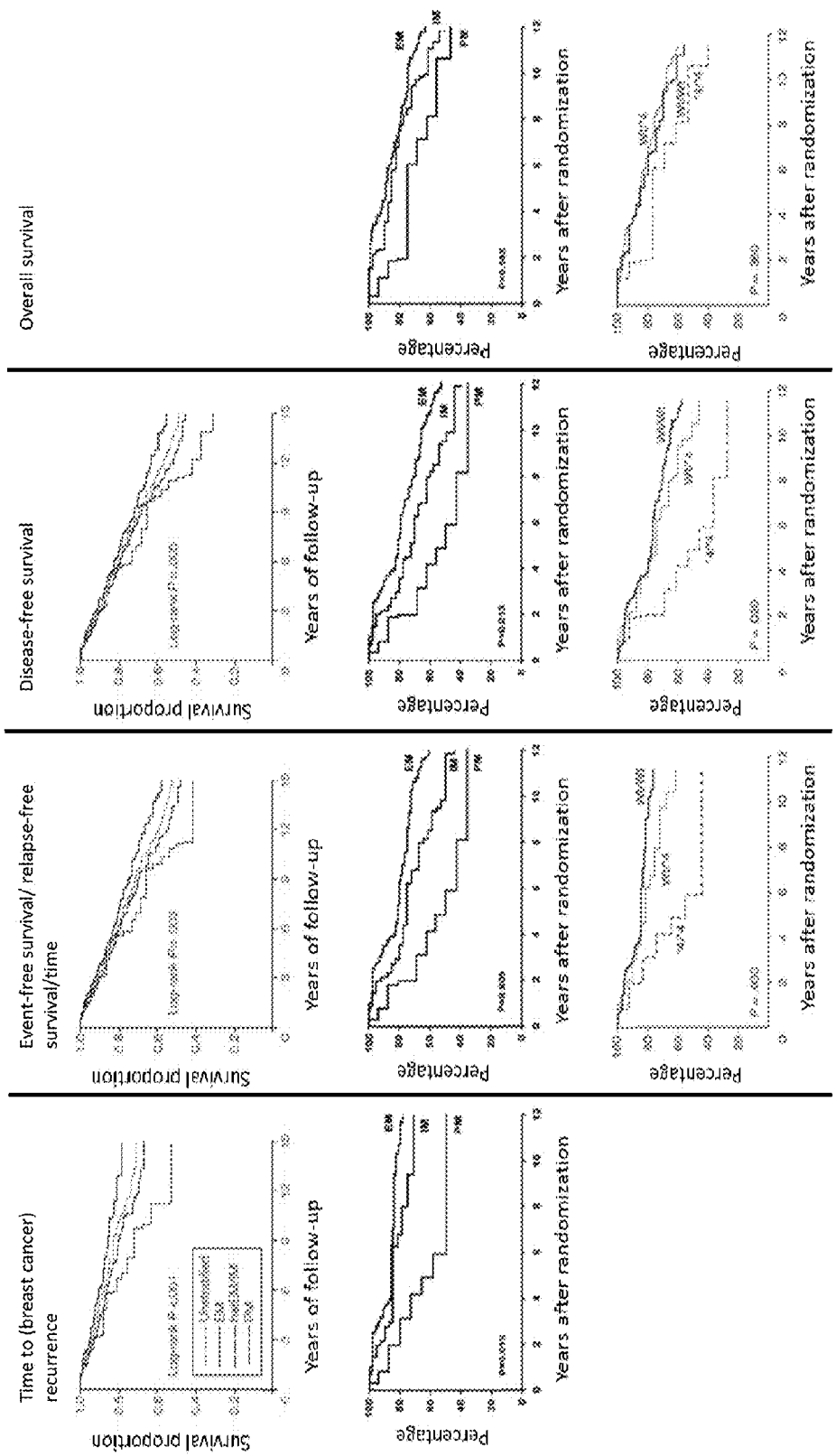
FIG. 3 shows relapse-free survival curves (Kaplan-Meier) for breast cancer patients under tamoxifen therapy according to the cytochrome P450 (CYP) 2D6 extensive metabolizer (EM), intermediate metabolizer (IM), or poor metabolizer (PM) genotype or phenotype.

There is now a range of studies which provides evidence for the dependency of the therapeutic success of tamoxifen on the CYP2D6 genotype or phenotype [Bijl, M., R. van Schaik, et al. (2009). "The CYP2D6*4 polymorphism affects breast cancer survival in tamoxifen users." Breast Cancer Res Treat 118(1): 125-130.; Bonanni, B., D. Macis, et al. (2006). "Polymorphism in the CYP2D6 Tamoxifen-Metabolizing Gene Influences Clinical Effect but Not Hot Flashes: Data From the Italian Tamoxifen Trial." Journal of Clinical Oncology 24(22): 3708-3709.; Brauch, H., W. Schroth, et al. (2008). "Clinical Relevance of CYP2D6 Genetics for Tamoxifen Response in Breast Cancer." Breast Care (Basel) 3(1): 43-50.; Brauch, H. B., W. Schroth, et al. (2011). "CYP2D6 and Tamoxifen: Awaiting the Denouement." Journal of Clinical Oncology 29(34): 4589-4590.; Goetz, M. P., A. Kamal, et al. (2008). "Tamoxifen pharmacogenomics: the role of CYP2D6 as a predictor of drug response." Clin Pharmacol Ther 83(1): 160-166.; Goetz, M. P., S. K. Knox, et al. (2007). "The impact of cytochrome P450 2D6 metabolism in women receiving adjuvant tamoxifen." Breast Cancer Res Treat 101(1): 113-121.; Goetz, M. P., J. M. Rae, et al. (2005). "Pharmacogenetics of tamoxifen biotransformation is associated with clinical outcomes of efficacy and hot flashes." J Clin Oncol 23(36): 9312-9318.; Ingelman-Sundberg, M., S. C. Sim, et al. (2007). "Influence of cytochrome P450 polymorphisms on drug therapies: pharmacogenetic, pharmacoepigenetic and clinical aspects." Pharmacol Ther 116(3): 496-526.; Newman, W. G., K. D. Hadfield, et al. (2008). "Impaired tamoxifen metabolism reduces survival in familial breast cancer patients." Clin Cancer Res 14(18): 5913-5918.; Schroth, W., L. Antoniadou, et al. (2007). "Breast cancer treatment outcome with adjuvant tamoxifen relative to patient CYP2D6 and CYP2C19 genotypes." J Clin Oncol 25(33): 5187-5193.; Schroth, W., M. P. Goetz, et al. (2009). "Association between CYP2D6 polymorphisms and outcomes among women with early stage breast cancer treated with tamoxifen." JAMA 302(13): 1429-1436; Goetz, M. P., et al., CYP2D6 metabolism and patient outcome in the Austrian Breast and Colorectal Cancer Study Group trial (ABCSG) 8. Clin Cancer Res, 2013. 19(2): p. 500-7.; Brauch, H., et al., Tamoxifen Use in Postmenopausal Breast Cancer: CYP2D6 Matters. J Clin Oncol, 2012.]. According to these studies, PMs consequently benefit distinctly less from tamoxifen therapy than IMs, and these in turn less than EMs or UMs, and this is reflected, for example, in published relapse-free survival curves (so-called Kaplan-Meier plots). Examples of such published plots are shown in FIG. 3. In the past, these study results were interpreted to mean that the main action in breast cancer therapy with tamoxifen originates from its metabolite endoxifen (tamoxifen is occasionally also referred to in the literature as a "prodrug" [Goetz, M. P., A. Kamal, et al. (2008). "Tamoxifen pharmacogenomics: the role of CYP2D6 as a predictor of drug response." Clin Pharmacol Ther 83(1): 160-166.]). Experts are also currently discussing the proposal of whether endoxifen should not be directly administered instead of tamoxifen, and initial studies have been published which have the goal of authorization of pure endoxifen as an agent for breast cancer therapy [Ahmad, A., S. M. Ali, et al. (2010). "Orally administered endoxifen is a new therapeutic agent for breast cancer." Breast Cancer Res Treat 122(2): 579-584.; Ahmad, A., S. Shahabuddin, et al. (2010). "Endoxifen, a new cornerstone of breast cancer therapy: demonstration of safety, tolerability, and systemic bioavailability in healthy human subjects." Clin Pharmacol Ther 88(6): 814-817.].

Similarly, there have been discussions for some time among experts [de Graan, A. J., S. F. Teunissen, et al. (2011). "Dextromethorphan as a phenotyping test to predict endoxifen exposure in patients on tamoxifen treatment." J Clin Oncol 29(24): 3240-3246.; Irvin, W. J., Jr., C. M. Walko, et al. (2011). "Genotype-Guided Tamoxifen Dosing Increases Active Metabolite Exposure in Women With Reduced CYP2D6 Metabolism: A Multicenter Study." J Clin Oncol 29(24): 3232-3239.; Brauch, H., W. Schroth, et al. (2008). "Clinical Relevance of CYP2D6 Genetics for Tamoxifen Response in Breast Cancer." Breast Care (Basel) 3(1): 43-50.; Lim, J. S., X. A. Chen, et al. (2011). "Impact of CYP2D6, CYP3A5, CYP2C9 and CYP2C19 polymorphisms on tamoxifen pharmacokinetics in Asian breast cancer patients." Br J Clin Pharmacol 71(5): 737-750.] as to whether patients should not be genotyped or phenotyped prior to tamoxifen treatment in order to restrict administration to the EMs and UMs, who benefit more (and so patients with the CYP2D6 PM and IM genotype or phenotype would have to manage without this inherently important treatment option). A further therapy strategy which is currently being discussed is that of increasing the dose of tamoxifen on the basis of genotype or phenotype in order to achieve, in patients of the CYP2D6 IM and PM phenotype, similar endoxifen concentrations as are achieved in CYP2D6 EM patients under normal tamoxifen therapy. In this connection, one study shows that this approach might possibly be a solution for CYP2D6 IM patients, but for patients of the CYP2D6 PM phenotype, comparable concentrations of endoxifen were definitely not achieved. Consequently, this option is not conceivable for patients of the CYP2D6 PM phenotype [Irvin, W. J., Jr., C. M. Walko, et al. (2011). "Genotype-Guided Tamoxifen Dosing Increases Active Metabolite Exposure in Women With Reduced CYP2D6 Metabolism: A Multicenter Study." J Clin Oncol 29(24): 3232-3239.].

According to the latest scientific knowledge, it has to be assumed that the positive action of tamoxifen in ER+ breast cancer can be attributed to the combination of the active components. Without doubt, tamoxifen itself has an antioestrogenic (and thus cancer-inhibiting) action, as do the two primary metabolites 4-hydroxytamoxifen and N-desmethyltamoxifen, which would not circulate in the plasma of the patient if endoxifen were administered, and it has to be assumed that the entire action of tamoxifen therapy is only achieved through the interplay of the parent substance and its active metabolites [V. C. Craig, Long-Term Tamoxifen Treatment for Breast Cancer, S. 32, Allen, K. E., E. R. Clark, et al. (1980). "Evidence for the metabolic activation of non-steroidal antioestrogens: a study of structure-activity relationships." Br J Pharmacol 71(1): 83-91.; Kemp, J. V., H. K. Adam, et al. (1983). "Identification and biological activity of tamoxifen metabolites in human serum." Biochem Pharmacol 32(13): 2045-2052.]. Consequently, it is doubtful whether exclusive endoxifen therapy can be a meaningful alternative to tamoxifen therapy; on the contrary, it has to be assumed that sole endoxifen administration is not an appropriate measure against the CYP2D6-dependence of tamoxifen therapy in oestrogen receptor-positive breast cancer.

The scientific prior art relating to tamoxifen therapy in breast cancer is very well documented. Although it concerns a relatively old substance, the CYP2D6 genotype- or phenotype-dependence of tamoxifen therapy is the subject of current research and lively discussions in the specialist field.

There was therefore the specific need for a tamoxifen treatment which takes into account the CYP2D6 genotype or phenotype and which enables patients of the CYP2D6 IM and PM phenotype to achieve endoxifen concentrations similar to those achieved in CYP2D6 EM patients under normal tamoxifen therapy and might accordingly also lead to promising therapy in the PMs and IMs in the form of breast cancer risk minimization.

To achieve the object, the present invention proposes combined administration of tamoxifen and endoxifen in a pharmaceutical formulation, more particularly in a fixed-dose combination (FDC). In a preferred embodiment, the formulation according to the invention, more particularly the FDC, is dosed in a genotype- or phenotype-specific manner.

FDCs consisting of two or more substances which are not related to one another like parent substance and metabolite are known according to the prior art and are, for example, used successfully in HIV therapy, type 2 diabetes therapy, hypertension therapy, hyperlipidaemia therapy or in the therapy of malaria and tuberculosis [Anvikar, A. R., B. Sharma, et al. (2012). "Artesunate-amodiaquine fixed dose combination for the treatment of Plasmodium falciparum malaria in India." Malar J 11(1): 97. Ayede, I. A., A. G. Falade, et al. (2010). "An open randomized clinical trial in comparing two artesunate-based combination treatments on Plasmodium falciparum malaria in Nigerian children: artesunate/sulphamethoxypyrazine/pyrimethamine (fixed dose over 24 hours) versus artesunate/amodiaquine (fixed dose over 48 hours)." Malar J 9: 378., Bramlage, P., W. P. Wolf, et al. (2010). "Effectiveness and tolerability of a fixed-dose combination of olmesartan and amlodipine in clinical practice." Vasc Health Risk Manag 6: 803-811., Gadzhanova, S., M. Gillies, et al. (2011). "Fixed dose combination diabetes medicines—usage in the Australian veteran population." Aust Fam Physician 40(10): 811-815., Honda, M., M. Ishisaka, et al. (2011). "Open-label randomized multicenter selection study of once daily antiretroviral treatment regimen comparing ritonavir-boosted atazanavir to efavirenz with fixed-dose abacavir and lamivudine." Intern Med 50(7): 699-705., Kauf, T. L., K. L. Davis, et al. (2012). "Spillover adherence effects of fixed-dose combination HIV therapy." Patient Prefer Adherence 6: 155-164., Kim, S. H., K. H. Ryu, et al. (2011). "Efficacy of fixed-dose amlodipine and losartan combination compared with amlodipine monotherapy in stage 2 hypertension: a randomized, double blind, multicenter study." BMC Res Notes 4: 461., Mathew, J. L. (2009). "Fixed dose drug combination for treatment of tuberculosis." Indian Pediatr 46(10): 877-880., Mengden, T., R. Hubner, et al. (2011). "Office and ambulatory blood pressure control with a fixed-dose combination of candesartan and hydrochlorothiazide in previously uncontrolled hypertensive patients: results of CHILI CU Soon." Vasc Health Risk Manag 7: 761-769., Mengden, T., S. Uen, et al. (2009). "Management of hypertension with fixed dose combinations of candesartan cilexetil and hydrochlorothiazide: patient perspectives and clinical utility." Vasc Health Risk Manag 5: 1043-1058., Okpechi, I. G., H. S. Schoeman, et al. (2011). "Achieving blood preSsure goals sTudy in uncontrolled hypeRtensive pAtients treated with a fixed-dose combination of ramipriL/hydrochlorothiazide: the ASTRAL study." Cardiovasc J Afr 22(2): 79-84., Reynolds, J. K. (2009). "Fixed-dose combination of sitagliptin and metformin for the treatment of type 2 diabetes." Diabetes Metab Syndr Obes 2: 127-134., Shiga, Y., S. Miura, et al. (2011). "Comparison of the efficacy and safety of single-pill fixed-dose combinations of losartan/hydrochlorothiazide and valsartan/hydrochlorothiazide in patients with hypertension (SALT-VAT study)." Intern Med 50(21): 2477-2483.].

The advantages compared to separate administration of two or more active ingredients are the simpler logistics, the reduced costs in manufacture and distribution, and (crucial in the case of tamoxifen/endoxifen) improved compliance in the patients.

A fixed-dose combination, more particularly a genotype- or phenotype-specific FDC, containing a parent substance and one or more potential metabolites and serving to compensate for genotype- or phenotype-related variability of the metabolite concentration is not known according to the prior art. Similarly, a fixed-dose combination containing a parent substance and one or more potential metabolites and serving to compensate for "phenotype-copying" related variability of the metabolite concentration is not known according to the prior art. Here, "phenotype-copying" means that, as a result of simultaneous administration of one medicament which is converted into one/more active metabolites via an enzyme and one potent enzyme inhibitor or enzyme inducer which inhibits or induces said conversion, the original phenotype of the patient is converted into another on the basis of the interaction between enzyme and enzyme inhibitor or enzyme inducer. A plausible example here is the administration of a potent CYP2D6 inhibitor (for example, paroxetine) to a patient of the CYP2D6 EM phenotype who is simultaneously receiving tamoxifen. As a result of the active ingredient-mediated (for example, paroxetine) CYP2D6 inhibition, the original CYP2D6 EM patient is in effect an IM or PM and has, accordingly, lower endoxifen concentrations, the active secondary metabolite of tamoxifen [Borges, S., Z. Desta, et al. (2006). "Quantitative effect of CYP2D6 genotype and inhibitors on tamoxifen metabolism: implication for optimization of breast cancer treatment." Clin Pharmacol Ther 80(1): 61-74.; Jin, Y., Z. Desta, et al. (2005). "CYP2D6 Genotype, Antidepressant Use, and Tamoxifen Metabolism During Adjuvant Breast Cancer Treatment." Journal of the National Cancer Institute 97(1): 30-39., Stearns, V., M. D. Johnson, et al. (2003). "Active tamoxifen metabolite plasma concentrations after coadministration of tamoxifen and the selective serotonin reuptake inhibitor paroxetine." J Natl Cancer Inst 95(23): 1758-1764.].

Instead of breast cancer therapy purely with endoxifen, the approach involving a combined administration according to the invention of tamoxifen and endoxifen is advantageous in those patients who are not sufficiently able to form endoxifen (i.e. CYP2D6 PMs and IMs), owing to the demonstrated efficacy of tamoxifen, N-desmethyltamoxifen and 4-hydroxytamoxifen. The goal of such a combined administration should be to compensate for the genotype- or phenotype-related reduced formation of endoxifen by administration of an appropriate endoxifen dose and, at the same time, to adapt the dose of tamoxifen if necessary such that PMs and IMs achieve steady-state plasma concentrations of tamoxifen, N-desmethyltamoxifen, 4-hydroxytamoxifen and endoxifen comparable to EMs or UMs under sole tamoxifen administration.

Figure 11:
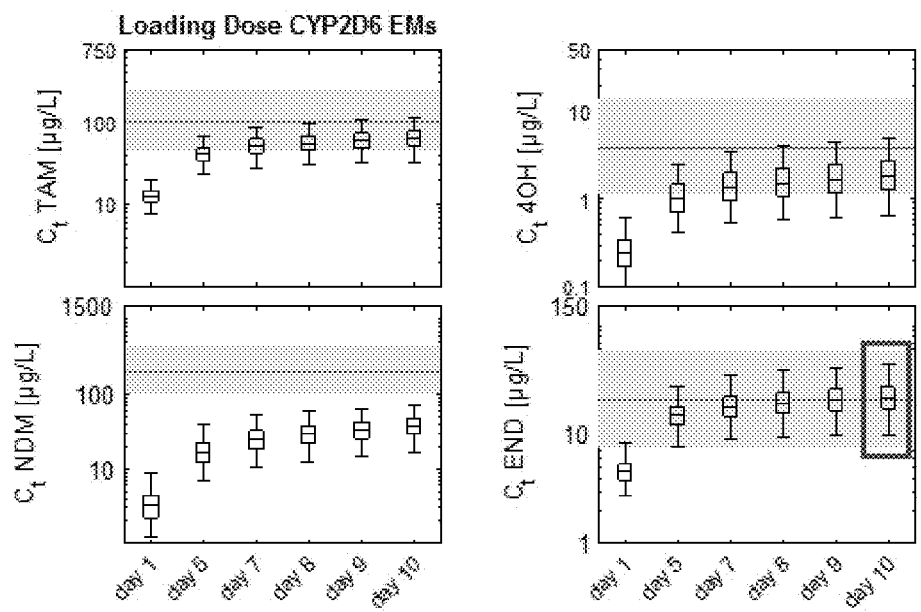
FIG. 11 shows the result of the loading dose study using PK-Sim® as per the method according to the invention for the simultaneous administration of tamoxifen and endoxifen in CYP2D6 EM patients.
Figure 12:
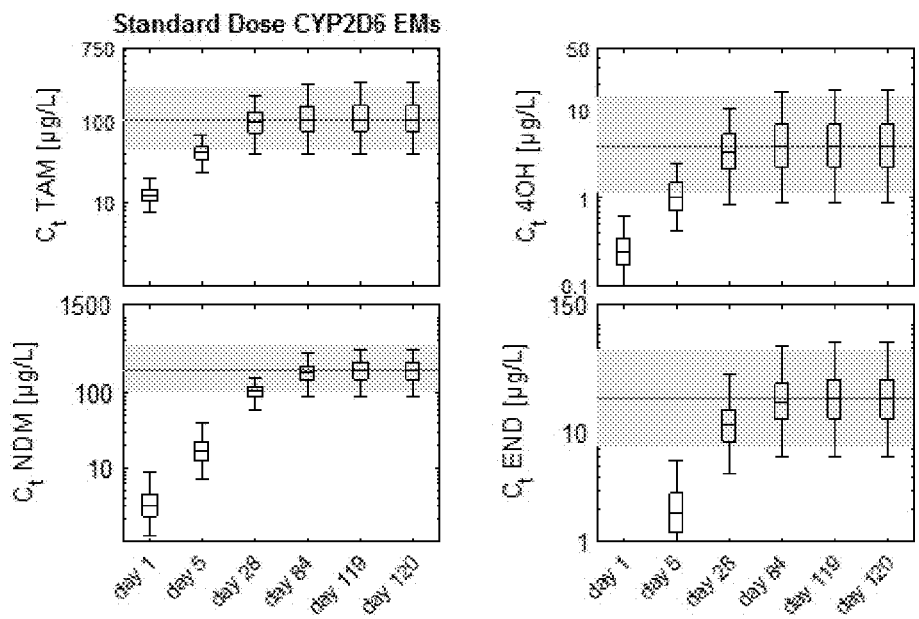
FIG. 12 shows the result of the loading-dose control study using PK-Sim® as per the method according to the invention for the simultaneous administration of tamoxifen and endoxifen in CYP2D6 EM patients.

Beyond the aforementioned advantages of the tamoxifen-endoxifen FDCs for CYP2D6 IMs and PMs, application of the proposed fixed combination, more particularly 20 mg of tamoxifen and 3 mg of endoxifen, may also be advantageous under certain circumstances in CYP2D6 EMs and IMs. For example, in the initial phase of tamoxifen therapy, the period until attainment of the desired equilibrium concentration (also termed steady-state concentration) can be considerably shortened. In the case of the standard therapeutic dosage of 20 mg of tamoxifen, the steady-state concentration of endoxifen in an example population consisting of European patients of the CYP2D6 EM genotype or phenotype is achieved after about 80 days [Fabian C, Sternson L, El-Serafi M, Cain L, Hearne E.; Clinical pharmacology of tamoxifen in patients with breast cancer: correlation with clinical data. Cancer. 1981 August 15; 48(4):876-82.; Jin Y, Desta Z, Stearns V, Ward B, Ho H, Lee K H, Skaar T, Storniolo A M, Li L, Araba A, Blanchard R, Nguyen A, Ullmer L, Hayden J, Lemler S, Weinshilboum R M, Rae J M, Hayes D F, Flockhart D A.; CYP2D6 genotype, antidepressant use, and tamoxifen metabolism during adjuvant breast cancer treatment. J Natl Cancer Inst. 2005 Jan. 5; 97(1):30-9.; Fuchs W S, Leary W P, van der Meer M J, Gay S, Witschital K, von Nieciecki A.; Pharmacokinetics and bioavailability of tamoxifen in postmenopausal healthy women. Arzneimittelforschung. 1996 April; 46(4):418-22.]. By contrast, if the tamoxifen therapy is initially carried out with the proposed fixed combination, it is shown, on the basis of the PBPK model, that the effective steady-state concentrations of endoxifen appear distinctly faster, viz. after just 9 days, as shown in FIGS. 11 and 12.

The advantages of the fixed tamoxifen-endoxifen combination that are shown for the start of breast cancer therapy with tamoxifen can, in addition, also be transferred to the frequently occurring real-life situation of continuous medicament intake being interrupted (also referred to as non-compliance). Such non-compliance is known in tamoxifen patients and well documented. Poor compliance is associated with a possible poorer response to tamoxifen therapy [Barron, T. I., et al., Early discontinuation of tamoxifen: a lesson for oncologists. Cancer, 2007. 109(5): p. 832-9.; Dezentje, V. O., et al., Effect of concomitant CYP2D6 inhibitor use and tamoxifen adherence on breast cancer recurrence in early-stage breast cancer. J Clin Oncol, 2010. 28(14): p. 2423-9.; Friese, C. R., et al., Adjuvant endocrine therapy initiation and persistence in a diverse sample of patients with breast cancer. Breast Cancer Res Treat, 2013.; Hershman, D. L., et al., Early discontinuation and nonadherence to adjuvant hormonal therapy in a cohort of 8,769 early-stage breast cancer patients. J Clin Oncol, 2010. 28(27): p. 4120-8.; McCowan, C., et al., Cohort study examining tamoxifen adherence and its relationship to mortality in women with breast cancer. Br J Cancer, 2008. 99(11): p. 1763-8.; Partridge, A. H., Non-adherence to endocrine therapy for breast cancer. Ann Oncol, 2006. 17(2): p. 183-4.; Rae, J. M., et al., Cytochrome P450 2D6 activity predicts discontinuation of tamoxifen therapy in breast cancer patients. Pharmacogenomics J, 2009. 9(4): p. 258-64.; Ruddy, K. J. and A. H. Partridge, Adherence with adjuvant hormonal therapy for breast cancer. Ann Oncol, 2009. 20(3): p. 401-2.; Ziller, V., et al., Adherence to adjuvant endocrine therapy in postmenopausal women with breast cancer. Ann Oncol, 2009. 20(3): p. 431-6.].

In the event of a tamoxifen drug holiday, the plasma levels of tamoxifen and its active metabolites (thus, endoxifen too in particular) fall below the therapeutically effective threshold. Similar to the initial tamoxifen therapy, the fixed combination can likewise be advantageously used here in CYP2D6 EMs and IMs in order to speed up the renewed attainment of effective concentrations, as shown by the results of the simulations in FIGS. 15 to 18.

Therefore, the present invention firstly provides a pharmaceutical formulation containing a parent substance, the action of which is dependent on the quantity or the activity of expressed and/or inhibited/induced protein variants, enzyme variants, receptor variants or transporter variants, and one or more potential metabolites of the parent substance. In particular, the dosage of the formulation according to the invention is defined in a genotype- or phenotype-specific manner.

However, such a combined formulation of multiple pharmaceutically active substances is associated with difficulties. The main difficulty is that of determining the optimal endoxifen and tamoxifen dose which ensures the therapeutically effective steady-state plasma levels in CYP2D6 PMs and IMs.

Figure 4:
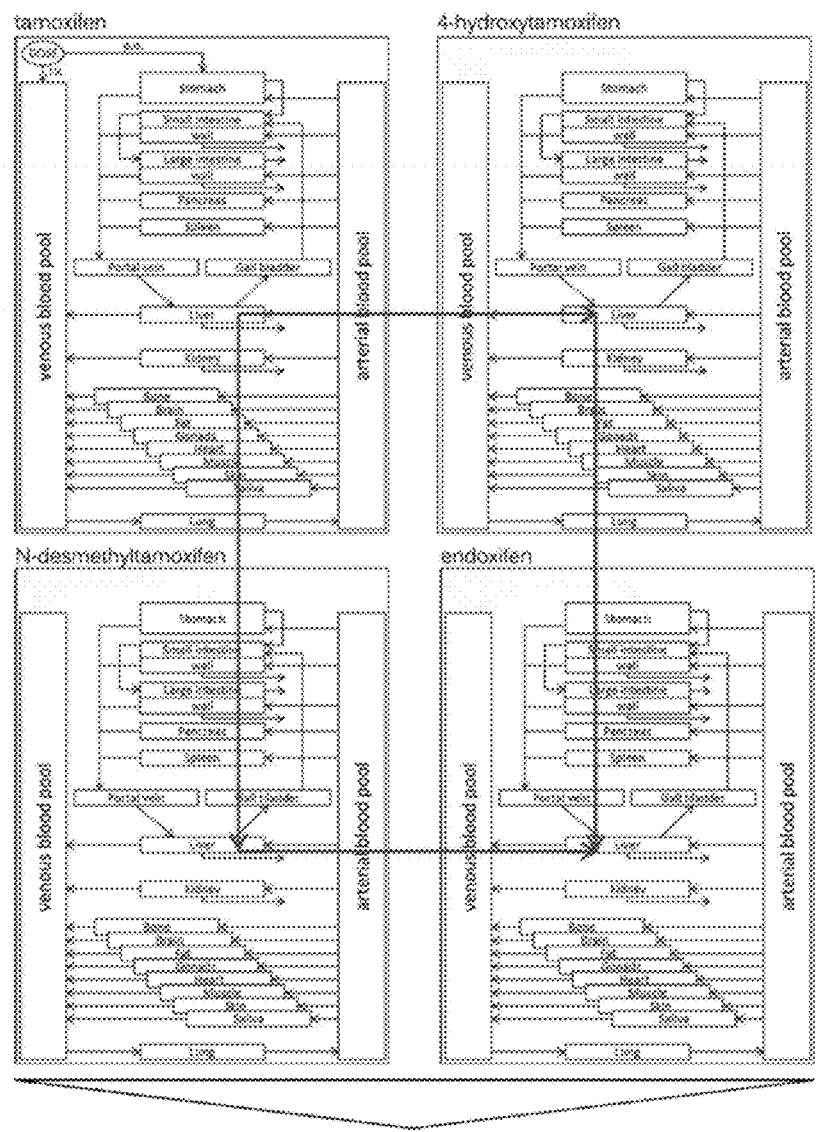
FIG. 4 shows a diagram of the compartments of the coupled physiologically based pharmacokinetic (PBPK) model as used in PK-Sim® for the simulation of the cytochrome P450 (CYP) 2D6 genotype- or phenotype-specific formation of N-desmethyltamoxifen, 4-hydroxytamoxifen and endoxifen following the administration of the parent substance tamoxifen or for the simulation of the simultaneous administration of tamoxifen and endoxifen according to the CYP2D6 genotype or phenotype and the resulting serum concentrations.
Figure 4:
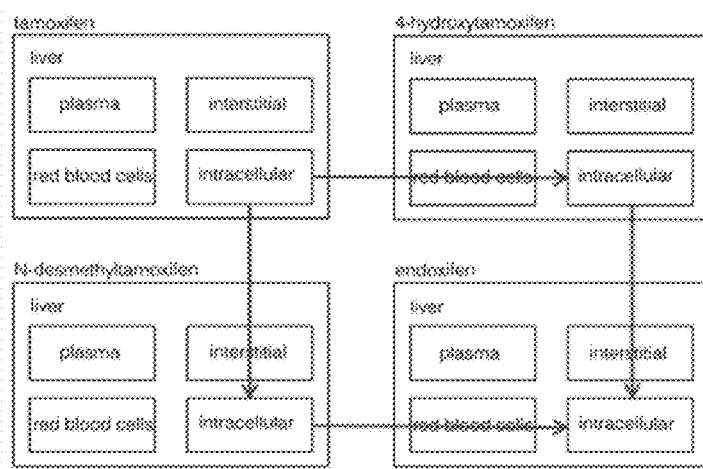

In the present invention, this further object was, by way of example, achieved by means of a method based on the use of a coupled physiologically based pharmacokinetic (PBPK) model for tamoxifen, 4-hydroxytamoxifen, N-desmethyltamoxifen and endoxifen. Said method and the corresponding commercially available model PK-Sim®/MoBi® are described in the applications WO2007/147539, WO05/116854 and WO 05/033982, the teachings of which are hereby integrated in this respect, and are used in the present invention to develop a method based on a coupled PBPK model. The development of the coupled PBPK model for tamoxifen, N-desmethyltamoxifen, 4-hydroxytamoxifen and endoxifen in CYP2D6 EMs and PMs has already been described [Dickschen, K., et al., Physiologically-based pharmacokinetic modeling of tamoxifen and its metabolites in women of different CYP2D6 phenotypes provides new insight into the tamoxifen mass balance. Frontiers in Pharmacology, 2012. 3.]. The method was subsequently used, by way of example, to optimize the tamoxifen and endoxifen doses in CYP2D6 PMs and IMs. The only difference between the published CYP2D6 PM model parameterization and the CYP2D6 IM parameterization additionally presented here is the factor used for CYP2D6 enzyme activity (IM: 0.62; PM 0.015 [Coller, J. K., N. Krebsfaenger, et al. (2002). "The influence of CYP2B6, CYP2C9 and CYP2D6 genotypes on the formation of the potent antioestrogen Z-4-hydroxy-tamoxifen in human liver." Br J Clin Pharmacol 54(2): 157-167.]). FIG. 4 shows a diagram of the coupled PBPK model for tamoxifen and its three active metabolites (N-desmethyltamoxifen, 4-hydroxytamoxifen, endoxifen).

Therefore, the present invention further provides a method for preparing a fixed-dose combination pharmaceutical formulation comprising a parent substance, the action of which is dependent on the amount or the activity of expressed and/or inhibited/induced protein variants, enzyme variants, receptor variants or transporter variants, and at least one metabolite of the parent substance, comprising the following steps:
   a) inputting of an organism, of its genotype or phenotype, of the parent substance and at least the metabolite of the parent substance, of an optimal reference steady-state plasma level for the parent substance for a reference genotype or reference phenotype in the case of delivery of the parent substance alone into an input module,
   b) forwarding of the data from a) into a calculation module comprising a substance data module, an organism data module, a genotype data module or a phenotype data module, and a physiologically based pharmacokinetic model, wherein the substance data module comprises data concerning the physicochemical and/or biochemical properties of the substance(s), the organism module comprises data concerning the compartments of the organism, and the genotype data module or phenotype data module comprises genotype- or phenotype-specific data,
   c) automatically selecting parent substance and metabolite-specific data from the substance data module,
   d) automatically selecting organism-specific data from the organism data module on the basis of input a),
   e) automatically selecting genotype- or phenotype-specific data from the genotype data module or phenotype data module,
   f) forwarding of the selected data from a) to e) into the physiologically based pharmacokinetic model,
   g) calculating, by means of the physiologically based pharmacokinetic model, an optimized dosage for the parent substance for the reference genotype or reference phenotype in order to attain the inputted optimal reference plasma level for the parent substance from a), h) calculating the reference steady-state plasma level for the metabolites (N-desmethyltamoxifen, 4-hydroxytamoxifen, endoxifen) for the reference genotype or reference phenotype in the case of administration of the dose of parent substance calculated in g), i) calculating a plasma level of the metabolite(s) that is reduced owing to the genotype or phenotype inputted in a) with respect to the corresponding reference plasma level in the case of administration of the dose of parent substance calculated in g), j) calculating a metabolite dose and a parent substance dose for the combined attainment of the reference plasma level for the metabolite(s) from h) and of the reference plasma level for the parent substance from a), k) outputting the metabolite dose and the parent substance dose for the fixed-dose combination pharmaceutical formulation via an output module, and/or l) forwarding the dose calculated in j) into an automated device for dosing medicaments.

In the present invention, automated devices for dosing medicaments mean devices for preparing dosage forms such as, for example, tablets, capsules, liquid dosage or elements thereof, and also apparatuses for measuring out the dosage, such as a balance, unit-dose systems known in the prior art, or a device for volumetrically or gravimetrically measuring out liquids.

Optionally, the calculation module additionally has an administration module which comprises data concerning dosage forms such as, for example, tablets, capsules, liquid dosage, or elements thereof. Said data usually comprise release properties of the dosage form, such as immediate, delayed release and also differentiated (e.g. by means of a layered active-ingredient distribution) or simultaneous release (e.g. by means of joint granulation) for combination formulations. In the input module, the dosage form can then be selectively defined, and the data concerning the corresponding dosage form are automatically selected from the administration module and forwarded to the physiologically based pharmacokinetic model.

The calculation module calculates the optimal medicament dose for the parent substance and the metabolite(s) and, where appropriate, an optimal dosing regimen. It consists of computer-implemented software and the hardware required to execute the program. The hardware is generally a commercially available PC. It is either directly connected to an input device, as in the case of a laptop computer with a built-in keyboard or chip card reader, or set up locally and connected to the input device (server). In principle, all common transmission technologies, both cable-based and wireless methods, are suitable and conceivable. Particularly preferred is wireless transmission of the patient information inputted via the handheld input module or the chip card reader.

The software makes it possible to manage all information relevant to calculating the optimal medicament dosage in one or more databases. In a preferred embodiment of the method, it is also possible to carry out the calculation of a patient-specific dose. This information relevant to calculating the medicament dose is usually divided into organism-specific, substance-specific, genotype- or phenotype-specific and preferably administration-specific data, and preferably stored, automatically retrievable, in corresponding data modules.

In a preferred embodiment which is particularly relevant to personalized medication, physiological (or anthropometric) information, pathological information, possibly information relating to additionally administered medicaments, so-called co-medication, are also likewise stored, automatically retrievable, in date modules as patient-specific data.

The substance data include, for example, lipophilicity, free plasma fraction, blood-plasma ratio, partition coefficients, permeability, volume of distribution, clearance, nature of the clearance, clearance proportions, nature of the excretion, dosing regimen, transporter substrate, pharmacokinetic and/or pharmacodynamic end-point and adverse effects.

Relevant medicament information is, more particularly, the recommended therapeutic dosage (according to information from the manufacturer), pharmacokinetic and/or pharmacodynamic end-point, clearance (total clearance as blood or plasma clearance in a reference population or a reference individual) and nature of the clearance (hepatic-metabolic, biliary, renal, etc.) and the proportions of the individual processes with respect to the total clearance, kinetic parameters of active transporters/receptors/enzymes if the medicament and/or its metabolite(s) is substrate for one or more active transporters/receptors/enzymes, and physicochemical and pharmacokinetic information such as, for example, lipophilicity, unbound fraction in plasma, plasma proteins to which the medicament and/or its metabolite(s) binds, blood-plasma distribution coefficient, or volume of distribution.

Empirical knowledge which, for example, can be obtained through the research of case studies can likewise additionally be part of the databases with substance information or information relating to co-medication.

Analogous to patient-specific information, relevant physiological or anthropometric and pathophysiological information is, for example, in each case age, gender, race, weight, height, body mass index, lean body mass, fat-free body mass, gene expression data, diseases, allergies, medication, renal function and hepatic function. Relevant pathophysiological information is, more particularly, diseases, allergies, renal function and hepatic function.

In the case of co-medication, the corresponding aforementioned information concerning all additional administered medicaments is part of the database relating to the co-medication.

The optimal dosage and, where appropriate, the optimal dosing regimen are calculated on the basis of the substance-specific data, organism-specific data and genotype- or phenotype-specific data possibly combined with the administration-specific data using a rational mathematical model for calculating the pharmacokinetic and pharmacodynamic behaviour of the substances to be administered (parent substance and metabolite(s)) on the basis of the information present in the databases. In this connection, rational mathematical models can, for example, be allometric scaling functions or physiologically based pharmacokinetic models.

In a preferred embodiment of the invention, a physiologically based pharmacokinetic/pharmacodynamic simulation model is used to calculate the individual dosage. Particularly preferred is the dynamically generated physiologically based simulation model described in detail in WO2005/633982.

A particular advantage when using the physiologically based simulation model from WO2005/633982 is the possibility of dynamically simulating simultaneous administration of multiple medicaments and their interaction. In this connection, dynamically means that, in the interaction, the kinetics of the two (possibly, also, more than two) interacting substances can be taken into consideration. This is advantageous over a static consideration in which, for example, an enzyme or a transporter is completely or partly inhibited in a time-independent manner, since the dynamic simulation allows optimization of the dosing regimen. A possible result of such optimization of the dosing regimen is, for example, the maintenance of a maximum interval of, for example, 12 hours (for a once daily administration) when administering two interacting substances in order to minimize the mutual influence.

Particularly suitable for carrying out the method according to the invention is the systems biology software suite consisting of PK-Sim® and MoBi® from Bayer Technology Services GmbH.

Processes such as protein inhibition or induction are known to be time-dependent, and so interaction effects based on said processes are also likewise time-dependent. In specific cases, these dynamic effects, which take place on a time scale of several days or weeks, can require the need for adaptation of the dose of a medicament over the course of therapy. A simple static consideration or merely the issuing of a warning to the handler in the case of immediate administration of mutually influencing medicaments, as are known according to the prior art, does not do justice to such complex, dynamic effects.

Exemplarily, the method according to the invention is capable of simulating the steady-state plasma levels of the four substances tamoxifen, 4-hydroxytamoxifen, N-desmethyltamoxifen and endoxifen in breast cancer patients with differing CYP2D6 genotypes or phenotypes according to the tamoxifen dose. Through an adaptation of the tamoxifen dose, which may be necessary, and a simultaneous simulation of administration of increasing endoxifen dosages, the model makes it possible to address the question of the optimal dosage of the two active ingredients in CYP2D6 IMs and PMs. In this specific case, the steady-state plasma levels are the pharmacologically critical parameter; the precise time course of the plasma concentration is secondary here. According to the invention, a suitable combination of substances is usually determined per genotype or phenotype, which combination compensates for the difference of said genotype or phenotype compared to the reference.

As dosage form, commercially available 20 mg tamoxifen tablet formulations with a once daily administration were taken as a basis, with none of the formulations being delayed or retarded on account of the formulation. Such a dosage form is, for example, described in the product information for Nolvadex® 20 mg film-coated tablets from Astra Zeneca or for Tamoxifen-Ratiopharm® 10 mg/20 mg/30 mg tablets from Ratiopharm, in section 6.1 in both cases.

In the present example, it was possible to show that a combination consisting of 20 mg of tamoxifen and 3 mg of endoxifen in CYP2D6 PMs leads to plasma levels of tamoxifen, N-desmethyltamoxifen, 4-hydroxytamoxifen and endoxifen that are comparable to those in the case of sole administration of 20 mg of tamoxifen in CYP2D6 EMs. In CYP2D6 IMs, the combination of 20 mg of tamoxifen and 1 mg of endoxifen was found to be optimal (FIGS. 5-7).

The present invention therefore further provides:
a fixed-dose combination formulation comprising 15-25 mg of tamoxifen and 0.25-5.0 mg of endoxifen.
More particularly:
a fixed-dose combination formulation for CYP2D6 IM patients comprising 15-25 mg of tamoxifen and 0.25-2.00 mg of endoxifen, more particularly 18-22 mg of tamoxifen and 0.5-1.5 mg of endoxifen, particularly preferably 20 mg of tamoxifen and 1.0 mg of endoxifen (FIG. 8 A b)) and a fixed-dose combination formulation for CYP2D6 PM patients comprising 15-25 mg of tamoxifen and 1.0-5.0 mg of endoxifen, more particularly 18-22 mg of tamoxifen and 2.0-4.0 mg of endoxifen, more particularly 20 mg of tamoxifen and 3.0 mg of endoxifen (FIG. 8 A c)).

Further components of the formulation according to the invention are known from the above mentioned prior art. For the preparation of a formulation according to the invention, use is made of the formulation from, inter alia, the product information for Nolvadex® 20 mg film-coated tablets from Astra Zeneca or for Tamoxifen-Ratiopharm® 10 mg/20 mg/30 mg tablets from Ratiopharm and Ahmad, A., et al., Endoxifen, a new cornerstone of breast cancer therapy: demonstration of safety, tolerability, and systemic bioavailability in healthy human subjects. Clin Pharmacol Ther, 2010. 88(6): p. 814-7 bzw. US 2009-0291134 A1.

In order to achieve higher endoxifen exposures in breast cancer patients, the tamoxifen dose was, in the past, also increased on an experimental basis. Instead of the 20 mg of tamoxifen per day, which is effective in CYP2D6 EM, up to 40 mg of tamoxifen per day as two individual doses were administered in CYP2D6 IMs and PMs. However, even this severe increase in the dose of the parent substance did not lead to the endoxifen concentrations observed in CYP2D6 EMs following a therapeutic dose of 20 mg of tamoxifen [Irvin, W. J., Jr., et al., Genotype-Guided Tamoxifen Dosing Increases Active Metabolite Exposure in Women With Reduced CYP2D6 Metabolism: A Multicenter Study. J Clin Oncol, 2011. 29(24): p. 3232-9.]. Therefore, a particular advantage of the described genotype- or phenotype-specific combined administration of tamoxifen and endoxifen is that the tamoxifen exposure in CYP2D6 IMs and PMs is not greatly elevated compared to the CP2D6 EMs (in contrast to the increase in tamoxifen dose that is currently being propagated in the scientific community).

However, since tamoxifen (and similarly the propagated non-fixed-dose combination therapy of tamoxifen and endoxifen in CYP2D6 PMs and IMs) must be taken once daily over a long period (typically 5 years), a second difficulty of a potential combination therapy is that of ensuring best possible compliance. It is known that compliance (and thus the success of treatment) in the case of a medicamentous therapy drops with the number of tablets which must be taken. For this reason, it is advantageous to combine tamoxifen and endoxifen to form an FDC. An FDC then contains in each case a defined dose of the two active ingredients, dependent on the CYP2D6 genotype or phenotype (PM or IM), in the form of a single dosage form (e.g. tablet or capsule).

Thus, a further preferred embodiment of the invention is in each case a genotype- or phenotype-specific fixed-dose combination of tamoxifen and endoxifen in the aforementioned ratios.

The approach shown using the example of tamoxifen/endoxifen can also be readily transferred to other combinations of parent substance plus one (or more) metabolites, the formation of which is influenced by genotypic or phenotypic particularities and by the phenomenon of "phenotype copying", which has already been mentioned above. More particularly, for the optimization of codeine action, an FDC, more precisely a genotype- or phenotype-specific FDC of codeine and morphine (the conversion of which from codeine is likewise catalysed by CYP2D6), would be applicable.

Examples of further potential candidates would be, inter alia: ezlopitant, donepezil, clopidogrel, cyclophosphamide, azathioprine, irinotecan, leflunomide, capecitabine, prasugrel, venlafaxine, losartan, tolterodine, tramadol, oxycodone, hydrocodone, doxorubicin, mycophenolate mofetil, estramustine, ifosfamide, gemcitabine, etoposide, terfenadine, methotrexate.

The described invention of a pharmaceutical formulation, preferably an FDC, containing a parent substance and one or more metabolites can be readily transferred to other active-ingredient candidates. In the tamoxifen-endoxifen example detailed above, the problem is the insufficient conversion of tamoxifen to endoxifen in patients having a CYP2D6 IM or PM phenotype. As shown exemplarily, the combination of the standard dose of the parent substance with a genotype- or phenotype-specific endoxifen dose for CYP2D6 IMs or for CYP2D6 PMs in a fixed combined pharmaceutical formulation can make up for this insufficiency and differences in the therapy response are eliminated.

Essentially, the principle of a genotype- or phenotype-specific pharmaceutical formulation, preferably an FDC, consisting of a parent substance and one or more metabolites can be firstly transferred to all parent substances which, owing to a polymorphic enzyme, protein, receptor or transporter, are converted into one or more active metabolites and/or bound and/or transported and/or develop their pharmacodynamic action.

A further example of the conversion of a parent substance into an active metabolite via a polymorphic enzyme is clopidogrel. Clopidogrel inhibits blood coagulation, after it has been converted into its active metabolite, by blocking ADP-dependent thrombocyte activation via the glycoprotein IIb/IIIa receptor complex. Clopidogrel is converted into its active metabolite via, inter alia, the polymorphic enzyme CYP2C19. CYP2C19 is subject to a pronounced genetic polymorphism. Similar to CYP2D6, CYP2C19 PMs can therefore be found in the population. Here, too, it is reasonable to suspect that patients having a CYP2C19 PM genotype or phenotype might not benefit sufficiently from therapy with clopidogrel [Simon T, Bhatt D L, Bergougnan L, Farenc C, Pearson K, Perrin L, Vicaut E, Lacreta F, Hurbin F, Dubar M.; Genetic polymorphisms and the impact of a higher clopidogrel dose regimen on active metabolite exposure and antiplatelet response in healthy subjects., Clin Pharmacol Ther. 2011 August; 90(2):287-95.; Lee J B, Lee K A, Lee K Y.; Cytochrome P450 2C19 polymorphism is associated with reduced clopidogrel response in cerebrovascular disease. Yonsei Med J. 2011 September; 52(5):734-8.; Kazui M, Nishiya Y, Ishizuka T, Hagihara K, Farid N A, Okazaki O, Ikeda T, Kurihara A.; Identification of the human cytochrome P450 enzymes involved in the two oxidative steps in the bioactivation of clopidogrel to its pharmacologically active metabolite. Drug Metab Dispos. 2010 January; 38(1):92-9.; Savi P, Pereillo J M, Uzabiaga M F, Combalbert J, Picard C, Maffrand J P, Pascal M, Herbert J M.; Identification and biological activity of the active metabolite of clopidogrel. Thromb Haemost. 2000 November, 84(5):891-6.; Cervinski M A, Schwab M C, Lefferts J A, Lewis L D, Lebel K A, Tyropolis A M, Pflueger S M, Tsongalis G J.; Establishment of a CYP2C19 genotyping assay for clinical use. Am J Clin Pathol. 2013 February, 139(2):202-7; Frelinger A L 3rd, Lee R D, Mulford D J, Wu J, Nudurupati S, Nigam A, Brooks J K, Bhatt D L, Michelson A D.; A randomized, 2-period, crossover design study to assess the effects of dexlansoprazole, lansoprazole, esomeprazole, and omeprazole on the steady-state pharmacokinetics and pharmacodynamics of clopidogrel in healthy volunteers. J Am Coll Cardiol. 2012 Apr. 3, 59(14):1304-11.; Gong I Y, Crown N, Suen C M, Schwarz U I, Dresser G K, Knauer M J, Sugiyama D, Degorter M K, Woolsey S, Tirona R G, Kim R B.; Clarifying the importance of CYP2C19 and PON1 in the mechanism of clopidogrel bioactivation and in vivo antiplatelet response. Eur Heart J. 2012 November, 33(22):2856-2464a.; Mega J L, Hochholzer W, Frelinger A L 3rd, Kluk M J, Angiolillo D J, Kereiakes D J, Isserman S, Rogers W J, Ruff C T, Contant C, Pencina M J, Scirica B M, Longtine J A, Michelson A D, Sabatine M S.; Dosing clopidogrel based on CYP2C19 genotype and the effect on platelet reactivity in patients with stable cardiovascular disease. JAMA. 2011 Nov. 23, 306(20):2221-8.; Zabalza M, Subirana I, Sala J, Lluis-Ganella C, Lucas G, Tomás M, Masiä R, Marrugat J, Brugada R, Elosua R.; Meta-analyses of the association between cytochrome CYP2C19 loss- and gain-of-function polymorphisms and cardiovascular outcomes in patients with coronary artery disease treated with clopidogrel. Heart. 2012 January; 98(2):100-8., Yamamoto K, Hokimoto S, Chitose T, Morita K, Ono T, Kaikita K, Tsujita K, Abe T, Deguchi M, Miyagawa H, Saruwatari J, Sumida H, Sugiyama S, Nakagawa K, Ogawa H., Impact of CYP2C19 polymorphism on residual platelet reactivity in patients with coronary heart disease during antiplatelet therapy. J Cardiol. 2011 March; 57(2):194-201.; Jin B, Ni H C, Shen W, Li J, Shi H M, Li Y.; Cytochrome P450 2C19 polymorphism is associated with poor clinical outcomes in coronary artery disease patients treated with clopidogrel. Mol Biol Rep. 2011 March; 38(3):1697-702., Shuldiner A R, O'Connell J R, Bliden K P, Gandhi A, Ryan K, Horenstein R B, Damcott C M, Pakyz R, Tantry U S, Gibson Q, Pollin T I, Post W, Parsa A, Mitchell B D, Faraday N, Herzog W, Gurbel P A.; Association of cytochrome P450 2C19 genotype with the antiplatelet effect and clinical efficacy of clopidogrel therapy. JAMA. 2009 Aug. 26, 302(8):849-57.; Sibbing D, Stegherr J, Latz W, Koch W, Mehilli J, Dörrler K, Morath T, Schömig A, Kastrati A, von Beckerath N.; Cytochrome P450 2C19 loss-of-function polymorphism and stent thrombosis following percutaneous coronary intervention. Eur Heart J. 2009 April, 30(8):916-22.; Hulot J S, Bura A, Villard E, Azizi M, Remones V, Goyenvalle C, Aiach M, Lechat P, Gaussem P.; Cytochrome P450 2C19 loss-of-function polymorphism is a major determinant of clopidogrel responsiveness in healthy subjects. Blood. 2006 Oct. 1, 108(7):2244-7.]. Using the concept according to the invention, it is possible too in this case to calculate a genotype- or phenotype-specific pharmaceutical formulation, preferably an FDC, consisting of clopidogrel and its active metabolite in order to make up for the insufficient formation of active metabolite in CYP2C19 PMs.

To determine the optimal reference steady-state plasma level, it is possible to use either determined data, or a pharmacokinetic model such as PK-Sim® and MoBi® which can calculate the plasma level after input of a reference dose.

Furthermore, the principle of a genotype- or phenotype-specific pharmaceutical formulation, preferably an FDC, consisting of a parent substance and one or more metabolites can be transferred to all parent substances which, by means of an enzyme, protein, receptor or transporter which can be inhibited/induced, are converted into one or more active metabolites and/or bound and/or transported and/or develop their pharmacodynamic action.

As already detailed above using the example of tamoxifen and the CYP2D6 inhibitor paroxetine, the required simultaneous administration of a pharmaceutical ingredient A and a pharmaceutical ingredient B, where A must be converted into an active metabolite via an enzyme in order to develop its entire action and B inhibits said enzyme, can in effect convert a patient from an EM genotype or phenotype into a PM genotype or phenotype. As a result of the medically indicated simultaneous administration of paroxetine, the patient is in effect converted into a CYP2D6 PM, which can, accordingly, convert less tamoxifen into endoxifen. Using the concept detailed above, it is likewise possible here to calculate a genotype- or phenotype-specific pharmaceutical formulation, preferably an FDC, consisting of tamoxifen and endoxifen which can make up for the insufficiency of endoxifen formation from tamoxifen owing to the inhibition of CYP2D6 caused by paroxetine.

Analogously, the concept according to the invention is applicable in the case of a required and medically indicated simultaneous administration of clopidogrel and the competitive CYP2C19 inhibitor omeprazole. A resulting reduced conversion of clopidogrel into its active metabolite can likewise be made up for, using the concept and method detailed above, by calculating a genotype- or phenotype-specific pharmaceutical formulation, preferably an FDC, consisting of clopidogrel and its active metabolite.

The concept explained above is also capable of compensating for a combination of a genetic polymorphism and an enzyme inhibition and/or enzyme induction which additively reduce/increase the same or different enzymes or proteins or receptors or transporters in terms of their activity. This is explained exemplarily using the example of a patient having a CYP2D6 PM genotype or phenotype who is receiving tamoxifen therapy and additionally requires the administration of paroxetine. The effect on the formation of endoxifen from tamoxifen via CYP2D6 can be taken into account by the principle detailed above and an optimal genotype- or phenotype-specific pharmaceutical formulation, preferably an FDC, consisting of tamoxifen and endoxifen can be calculated. Analogously, this can also be comprehended using the example of a patient having a CYP2C19 PM genotype or phenotype under clopidogrel therapy who now requires the administration of omeprazole.

FIGURES

The figures illustrate the inventive concept for tamoxifen therapy and show the results of the tamoxifen/endoxifen FDC dose finding using PK-Sim® as per the method according to the invention as an example, without restricting the concept to said example.

FIG. 1 shows an extract from the complex biotransformation scheme for tamoxifen in humans. About 90% of tamoxifen is metabolized to N-desmethyltamoxifen and about 7% to 4-hydroxytamoxifen. Endoxifen is formed from N-desmethyltamoxifen exclusively via the polymorphic cytochrome P450 (CYP) 2D6. The formation of 4-hydroxytamoxifen from tamoxifen occurs via the polymorphic CYP2D6 to an extent of about 50%. Thus, CYP2D6 is largely involved in the essential endoxifen formation steps [Coller, J. K., N. Krebsfaenger, et al. (2002). "The influence of CYP2B6, CYP2C9 and CYP2D6 genotypes on the formation of the potent antioestrogen Z-4-hydroxy-tamoxifen in human liver," Br J Clin Pharmacol 54(2): 157-1.67.; Desta, Z., B. A. Ward, et al. (2004). "Comprehensive evaluation of tamoxifen sequential biotransformation by the human cytochrome P450 system in vitro: prominent roles for CYP3A and CYP2D6." J Pharmacol Exp Ther 310(3): 1062-1075.; Kaku, T., K. Ogura, et al. (2004). "Quaternary ammonium-linked glucuronidation of tamoxifen by human liver microsomes and UDP-glucuronosyltransferase 1A4." Biochem Pharmacol 67(11): 2093-2102.; Murdter, T. E., W. Schroth, et al. (2011). "Activity levels of tamoxifen metabolites at the estrogen receptor and the impact of genetic polymorphisms of phase I and II enzymes on their concentration levels in plasma," Clin Pharmacol Ther 89(5): 708-717.; Nishiyama, T., K. Ogura, et al. (2002). "Reverse geometrical selectivity in glucuronidation and sulfation of cis- and trans-4-hydroxytamoxifens by human liver UDP-glucuronosyltransferases and sulfotransferases." Biochem Pharmacol 63(10): 1817-1830.; Sun, D., G. Chen, et al. (2006). "Characterization of tamoxifen and 4-hydroxytamoxifen glucuronidation by human UGT1A4 variants." Breast Cancer Res 8(4): R50.; Sun, a, A. K. Sharma, et al. (2007). "Glucuronidation of active tamoxifen metabolites by the human UDP glucuronosyltransferases." Drug Metab Dispos 35(11): 2006-2014.]

Figure 2:
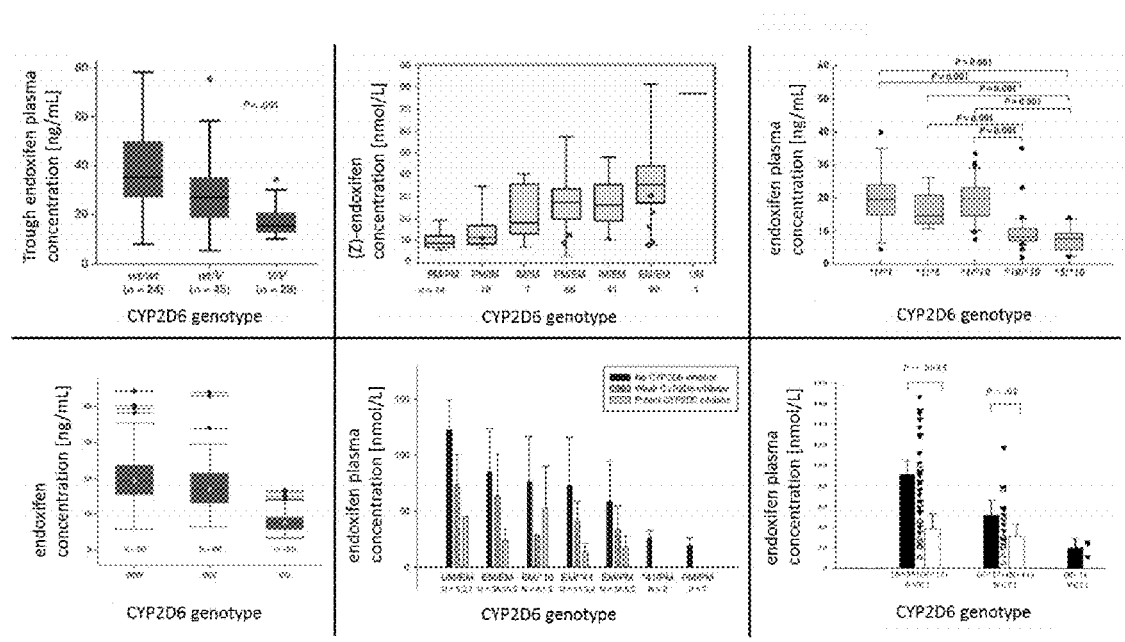
FIG. 2 shows cytochrome P450 (CYP) 2D6 genotype- or phenotype-dependent steady-state concentrations of endoxifen in the context of tamoxifen therapy in patients of the CYP2D6 extensive metabolizer (EM), intermediate metabolizer (IM) or poor metabolizer (PM) phenotype.

FIG. 2 shows cytochrome P450 (CYP) 2D6 genotype- or phenotype-dependent steady-state concentrations of endoxifen in the context of tamoxifen therapy in patients of the CYP2D6 extensive metabolizer (EM), intermediate metabolizer (IM) or poor metabolizer (PM) phenotype. A gene dosage effect of the endoxifen concentration is evident: patients having two functional CYP2D6 alleles (EMs) show a distinctly higher endoxifen exposure than patients having only one CYP2D6 functional allele (IMs) or no functional CYP2D6 allele (PM). [Figures from (from top left to bottom right): [Kiyotani, K., T. Mushiroda, et al. (2010). "Significant effect of polymorphisms in CYP2D6 and ABCC2 on clinical outcomes of adjuvant tamoxifen therapy for breast cancer patients." J Clin Oncol 28(8): 1287-1293.; Murdter, T. E., W. Schroth, et al. (2011). "Activity levels of tamoxifen metabolites at the estrogen receptor and the impact of genetic polymorphisms of phase I and II enzymes on their concentration levels in plasma." Clin Pharmacol Ther 89(5): 708-717.; Lim, J. S., X. A. Chen, et al. (2011). "Impact of CYP2D6, CYP3A5, CYP2C9 and CYP2C19 polymorphisms on tamoxifen pharmacokinetics in Asian breast cancer patients." Br J Clin Pharmacol 71(5): 737-750.; Lim, H. S., H. Ju Lee, et al. (2007). "Clinical implications of CYP2D6 genotypes predictive of tamoxifen pharmacokinetics in metastatic breast cancer." J Clin Oncol 25(25): 3837-3845.; Borges, S., Z. Desta, et al. (2006). "Quantitative effect of CYP2D6 genotype and inhibitors on tamoxifen metabolism: implication for optimization of breast cancer treatment." Clin Pharmacol Ther 80(1): 61-74.; Jin, Y., Z. Desta, et al. (2005). "CYP2D6 Genotype, Antidepressant Use, and Tamoxifen Metabolism During Adjuvant Breast Cancer Treatment" Journal of the National Cancer institute 97(1): 30-39.]

FIG. 3 shows relapse-free survival curves (Kaplan-Meier) for breast cancer patients under tamoxifen therapy according to the cytochrome P450 (CYP) 2D6 extensive metabolizer (EM), intermediate metabolizer (IM), or poor metabolizer (PM) genotype or phenotype. [Figures from (group 1 to 3): Schroth, W., M. P. Goetz, et at (2009). "Association between CYP2D6 polymorphisms and outcomes among women with early stage breast cancer treated with tamoxifen." JAMA 302(13): 1429-1435.; Goetz, M. P., S. K. Knox, et al. (2007). "The impact of cytochrome P450 2D6 metabolism in women receiving adjuvant tamoxifen." Breast Cancer Res Treat 101(1): 113-121.; Goetz, M. P., J. M. Rae, et al. (2005). "Pharmacogenetics of tamoxifen biotransformation is associated with clinical outcomes of efficacy and hot flashes." J Clin Oncol 23(36): 9312-9318.]

FIG. 4 shows a diagram of the compartments of the coupled physiologically based pharmacokinetic (PBPK) model as used in PK-Sim® for the simulation of the cytochrome P450 (CYP) 2D6 genotype- or phenotype-specific formation of N-desmethyltamoxifen, 4-hydroxytamoxifen and endoxifen following the administration of the parent substance tamoxifen or for the simulation of the simultaneous administration of tamoxifen and endoxifen according to the CYP2D6 genotype or phenotype and the resulting serum concentrations. In the intracellular compartment of the liver, tamoxifen gives rise to N-desmethyltamoxifen and 4-hydroxytamoxifen, and so the tamoxifen PBPK model acts as a developing function for the two primary metabolites. Analogously, the secondary metabolite endoxifen arises in the intracellular compartments of the PBPK models of N-desmethyltamoxifen and 4-hydroxytamoxifen.

Figure 5A:
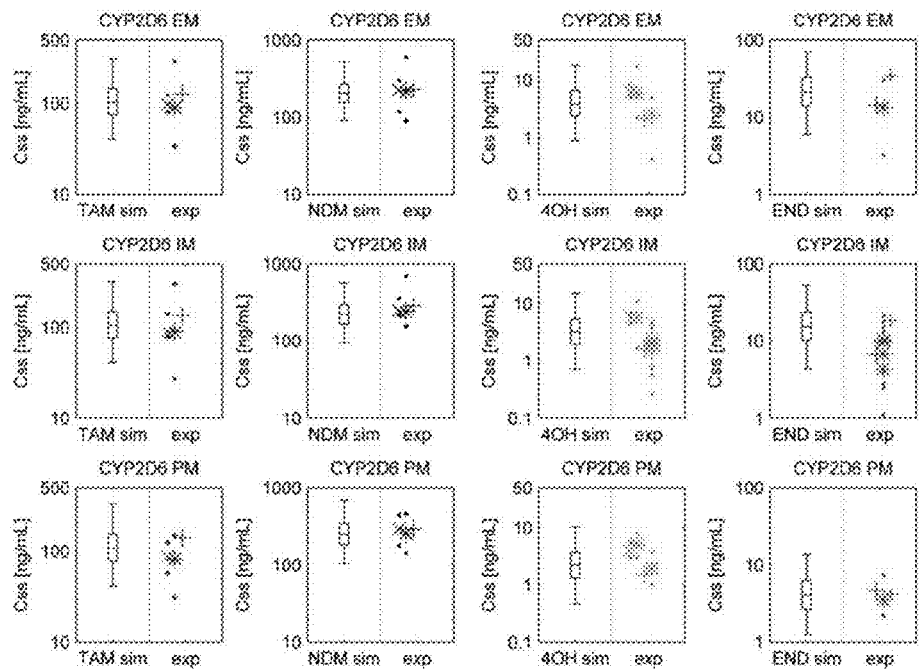
FIG. 5A shows coupled PBPK models for tamoxifen (TAM), N-desmethyltamoxifen (NDM), 4-hydroxytamoxifen (4OH), endoxifen (END) in CYP2D6 extensive metabolizer, intermediate metabolizer and poor metabolizer (EM/IM/PM) genotype or phenotype populations.
Figure 5B:
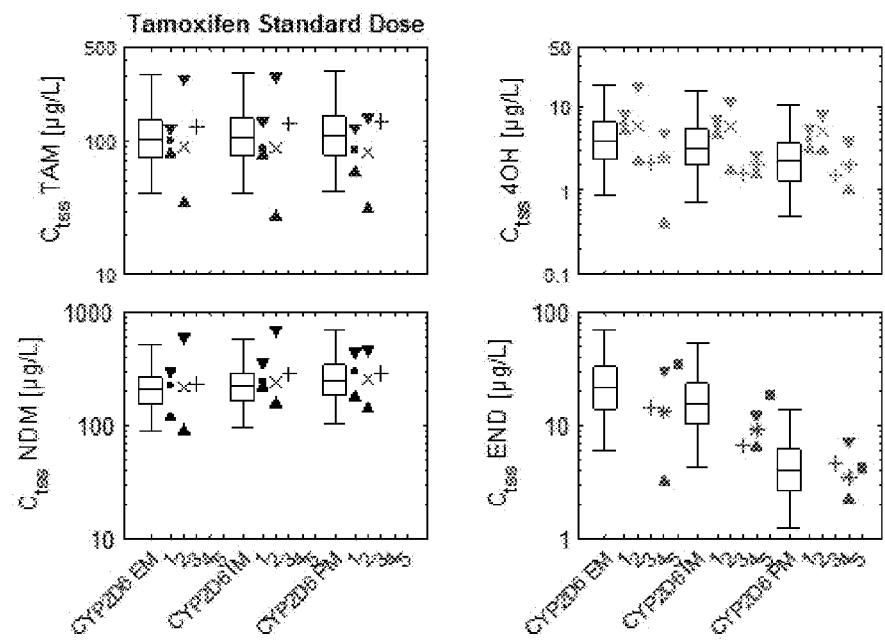
FIG. 5B shows an alternative depiction of the data shown in FIG. 5A.

FIG. 5A shows coupled PBPK models for tamoxifen (TAM), N-desmethyltamoxifen (NDM), 4-hydroxytamoxifen (4OH), endoxifen (END) in CYP2D6 extensive metabolizer, intermediate metabolizer and poor metabolizer (EM/IM/PM) genotype or phenotype populations. Steady-state plasma concentrations of tamoxifen, N-desmethyltamoxifen, 4-hydroxytamoxifen and endoxifen following once daily administration of 20 mg of tamoxifen over 1 year in example populations of European women of the cyotchrome P450 (CYP) 2D6 extensive metabolizer (EM), intermediate metabolizer (IM) and poor metabolizer (PM) genotype or phenotype. Box-and-whisker plots show the 5th, 25th, 50th, 75th, and 95th percentiles of the respective populations. Symbols represent experimental data for the model validation from left to right: Gjerde, J. Geisier, et al. (2010). "Associations between tamoxifen, estrogens, and FSH serum levels during steady state tamoxifen treatment of postmenopausal women with breast cancer." BMC Cancer 10: 313.; Gjerde, S., M. Hauglid, et al. (2008). "Effects of CYP2D6 and SULT1A1 genotypes including SULT1A1 gene copy number on tamoxifen metabolism." Ann Oncol 19(1): 56-61.; Madlensky, L., L. Natarajan, et al. (2011). "Tamoxifen metabolite concentrations, CYP2D6 genotype, and breast cancer outcomes." Clin Pharmacol Ther 89(5): 718-725.; Murdter, T. E., W. Schroth, et al. (2011). "Activity levels of tamoxifen metabolites at the estrogen receptor and the impact of genetic polymorphisms of phase I and II enzymes on their concentration levels in plasma." Clin Pharmacol Ther 89(5): 708-717.; Irvin, W. S., Jr., C. M. Walko, et al. (2011). "Genotype-Guided Tamoxifen Dosing Increases Active Metabolite Exposure in Women With Reduced CYP2D6 Metabolism: A Multicenter Study." J Clin Oncol 29(24): 3232-3239.]. FIG. 5B shows an alternative depiction.

Figure 6A:
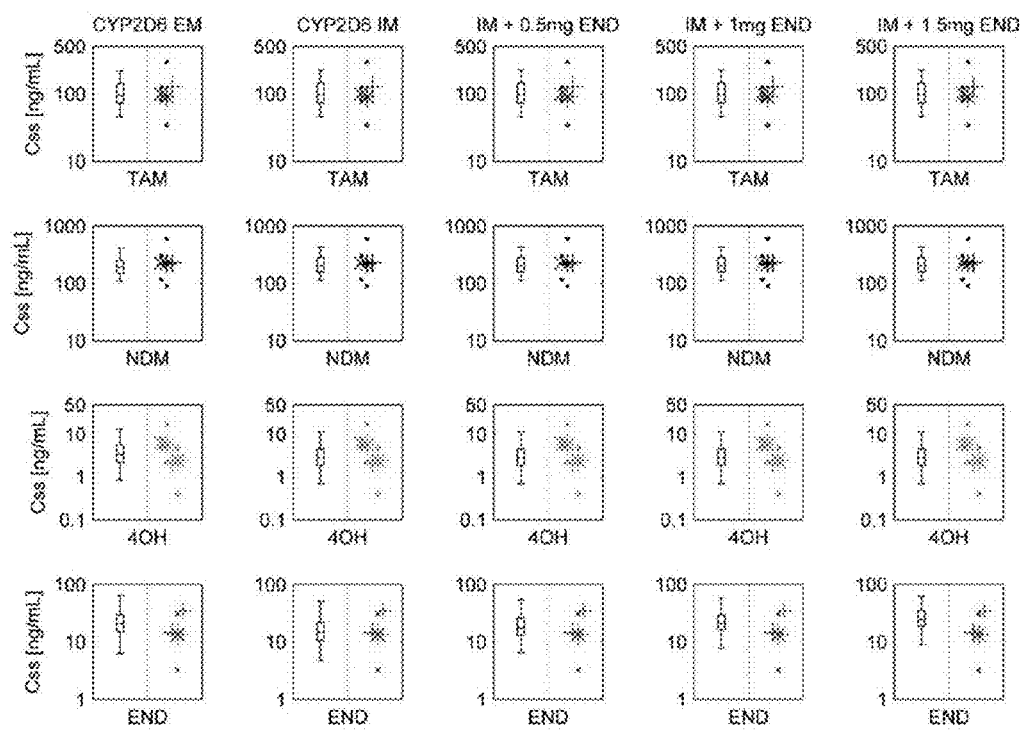
FIG. 6A shows the result of the endoxifen dose finding using PK-Sim® as per the method according to the invention for the simultaneous administration with tamoxifen in CYP2D6 IM patients.
Figure 6B:
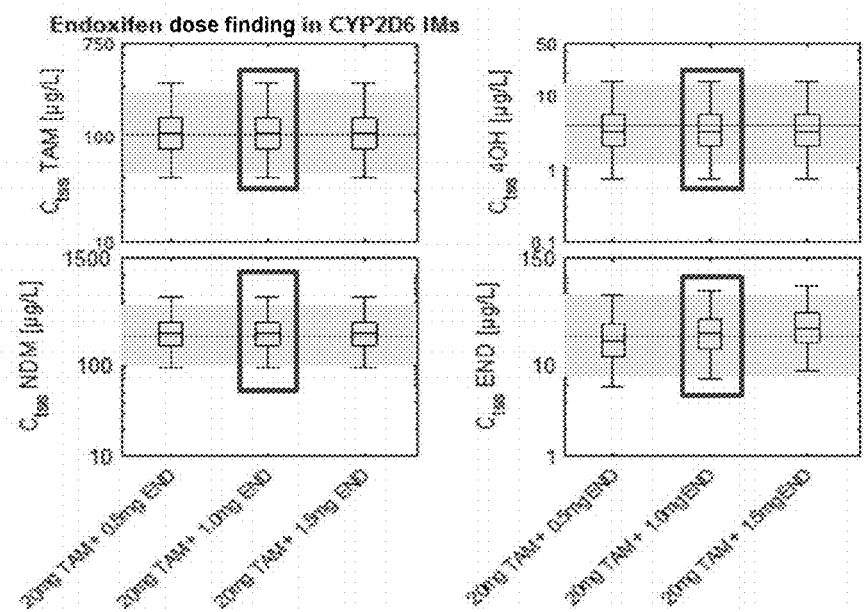
FIG. 6B shows an alternative depiction of the data shown in FIG. 6A.

FIG. 6A shows the result of the endoxifen dose finding using PK-Sim® as per the method according to the invention for the simultaneous administration with tamoxifen in CYP2D6 IM patients. FIG. 6A shows steady-state plasma concentrations of tamoxifen (TAM), N-desmethyltamoxifen (NDM), 4-hydroxytamoxifen (4OH) and endoxifen (END) following once daily administration of 20 mg of tamoxifen on a daily basis over 1 year in example populations of European patients with the cytochrome P450 (GYP) 2D6 extensive metaboliser (EM) or intermediate metabolizer (IM) genotype or phenotype in comparison with experimental data from patients of the CYP2D6 EM genotype or phenotype. Steady-state plasma concentrations of tamoxifen, N-desmethyltamoxifen, 4-hydroxytamoxifen and endoxifen in example populations of European patients of the CYP2D6 IM genotype or phenotype following simultaneous once daily administration of 20 mg of tamoxifen plus 0.5 mg or 1 mg or 1.5 mg of endoxifen, in addition, over 1 year. CYP2D6 IM patients who received 20 mg of tamoxifen plus 1 mg of endoxifen showed equivalent endoxifen concentrations with respect to CA/P2D6 EM patients who received 20 mg of tamoxifen once daily over 1 year. [From left to right: Gjerde, J. Geisler, et al, (2010). "Associations between tamoxifen, estrogens, and FSH serum levels during steady state tamoxifen treatment of postmenopausal women with breast cancer." BMC Cancer 10: 313.; Gjerde, J., M. Hauglid, et al. (2008). "Effects of CYP2D6 and SULT1A1 genotypes including SULT1A1 gene copy number on tamoxifen metabolism." Ann Oncol. 19(1): 56-61.; Madlensky, L., L. Natarajan, et al. (2011). "Tamoxifen metabolite concentrations, CYP2D6 genotype, and breast cancer outcomes." Clin Pharmacol Titer 89(5): 718-725.; Murdter, T. E., W. Schroth, et al. (2011). "Activity levels of tamoxifen metabolites at the estrogen receptor and the impact of genetic polymorphisms of phase I and II enzymes on their concentration levels in plasma." Clin Pharmacol Ther 89(5): 708-717.; Irvin, W. J., Jr., C. M. Walko, et al. (2011). "Genotype-Guided Tamoxifen Dosing Increases Active Metabolite Exposure in Women With Reduced CYP2D6 Metabolism: A Multicenter Study." J Clin Oncol 29(24): 3232-3239] FIG. 6B shows an alternative depiction. Serving as comparison are the determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). CYP2D6 IM patients who received 20 mg of tamoxifen plus 1 mg of endoxifen showed equivalent endoxifen concentrations with respect to CYP2D6 EM patients who received 20 mg of tamoxifen once daily over 1 year.

Figure 7A:
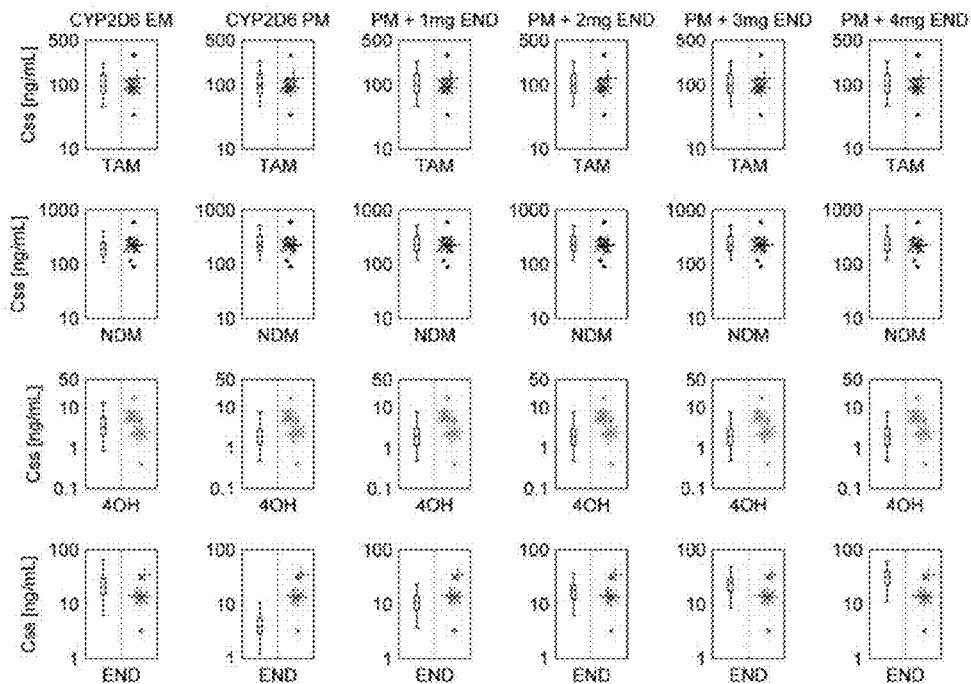
FIG. 7A shows the result of the endoxifen dose finding using PK-Sim® as per the method according to the invention for the simultaneous once daily administration with tamoxifen in CYP2D6 PM patients.
Figure 7B:
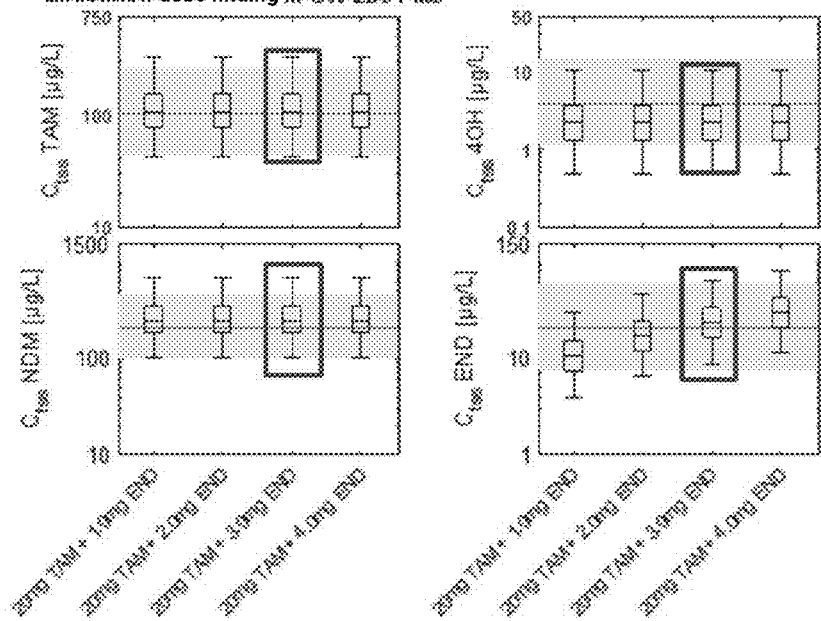
FIG. 7B shows an alternative depiction of the data shown in FIG. 7A.

FIG. 7A shows the result of the endoxifen dose finding using PK-Sim® as per the method according to the invention for the simultaneous once daily administration with tamoxifen in CA/P2D6 PM patients. FIG. 7A shows steady-state plasma concentrations of tamoxifen (TAM), N-desmethyltamoxifen (NDM), 4-hydroxytamoxifen (4OH) and endoxifen (END) following administration of 20 mg of tamoxifen once daily over 1 year in example populations of European patients with the cytochrome P450 (CYP) 2D6 extensive metabolizer (EM) or poor metabolizer (PM) genotype or phenotype in comparison with experimental data from patients of the CYP2D6 EM genotype or phenotype. Steady-state plasma concentrations of tamoxifen, N-desmethyltamoxifen, 4-hydroxytamoxifen and endoxifen in example populations of European patients of the CYP2D6 PM genotype or phenotype following simultaneous administration of 20 mg of tamoxifen plus 1 mg or 2 mg or 3 mg or 4 mg of endoxifen, in addition, over 1 year. CYP2D6 PM patients who received 20 mg of tamoxifen plus 3 mg of endoxifen showed equivalent endoxifen concentrations with respect to CYP2D6 EM patients who received 20 mg of tamoxifen once daily over 1 year, [From left to right: Gjerde, J. Geisler, et al. (2010). "Associations between tamoxifen, estrogens, and FSH serum levels during steady state tamoxifen treatment of postmenopausal women with breast cancer." BMC Cancer 10: 313.; Gjerde, J., M. Hauglid, et al. (2008). "Effects of CYP2D6 and SULT1A1 genotypes including SULT1A1 gene copy number on tamoxifen metabolism." Ann Oncol 19(1); 56-61.; Madiensky, L., L. Natarajan, et al. (2011). "Tamoxifen metabolite concentrations, CYP2D6 genotype, and breast cancer outcomes." Clin Pharmacol Ther 89(5): 718-725.; Murdter, T. E., W. Schroth, et al. (2011). "Activity levels of tamoxifen metabolites at the estrogen receptor and the impact of genetic polymorphisms of phase I and enzymes on their concentration levels in plasma." Clin Pharmacol Ther 89(5): 708-717.; Irvin, W. J., Jr., C. M. Walko, et al. (2011). "Genotype-Guided Tamoxifen Dosing Increases Active Metabolite Exposure in Women With Reduced CYP2D6 Metabolism: A Multicenter Study." J Clin Oncol 29(24): 3232-3239.] FIG. 7B shows an alternative depiction. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). CYP2D6 PM patients who received 20 mg of tamoxifen plus 3 mg of endoxifen showed equivalent endoxifen concentrations with respect to CYP2D6 EM patients who received 20 mg of tamoxifen once daily over 1 year.

FIG. 8 shows genotype- or phenotype-based dosing of tamoxifen and endoxifen as a loose combination (A) or as an FDC (B).

Figure 9:
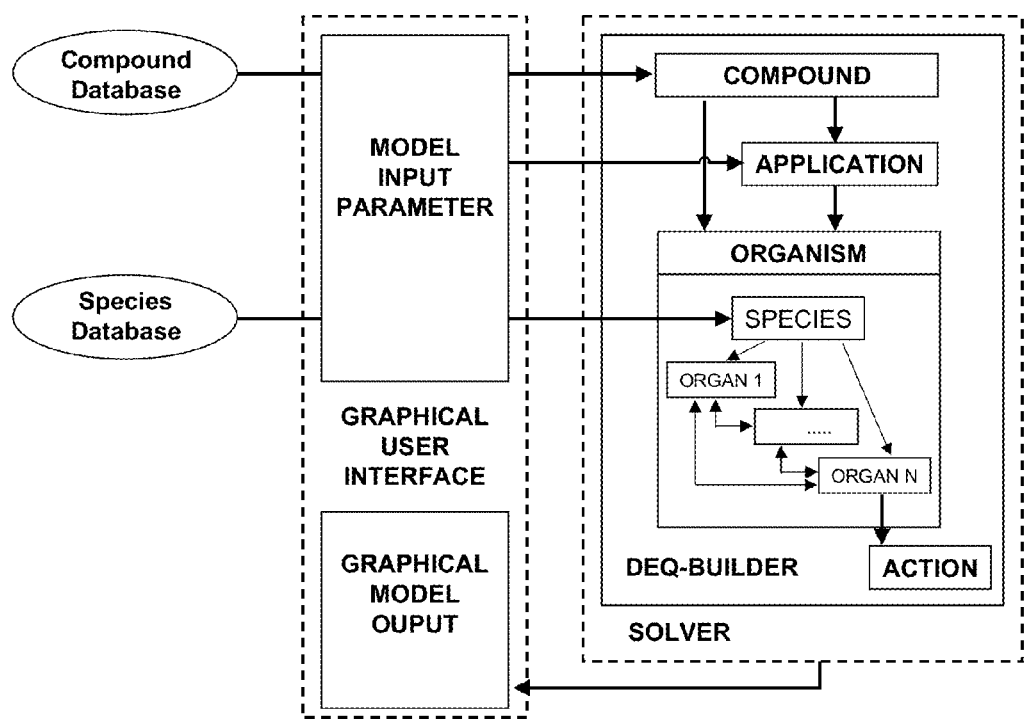
FIG. 9 shows a diagram of the modular design of PK-Sim®.
Figure 10:
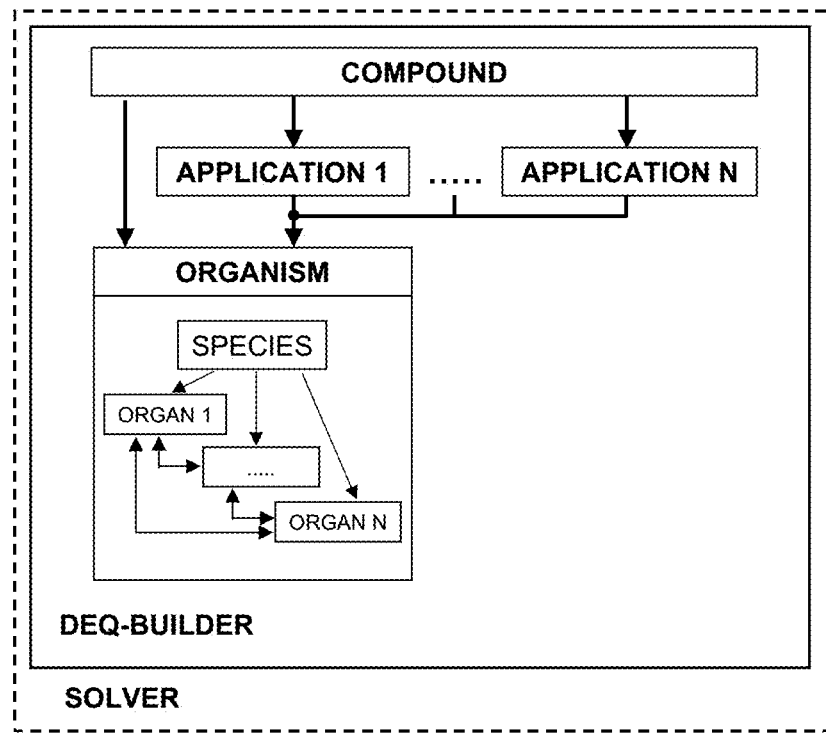
FIG. 10 shows another diagram of the modular design of PK-Sim®.

FIGS. 9 and 10 show a diagram of the modular design of PK-Sim®.

FIGS. 11 to 14 show the influence of an initial breast cancer therapy with the fixed combination of 20 mg of tamoxifen and 3 mg of endoxifen on the attainment of the endoxifen steady-state concentrations, systematically investigated by means of the PBPK model for CYP2D6 EMs and IMs.

FIG. 11 shows the result of the loading dose study using PK-Sim® as per the method according to the invention for the simultaneous administration of tamoxifen and endoxifen in CYP2D6 EM patients. FIG. 11 shows the trough plasma concentrations of tamoxifen (TAM), N-desmethyltamoxifen (NDM), 4-hydroxytamoxifen (4OH) and endoxifen (END) following simultaneous once daily administration of 20 mg of tamoxifen and 3 mg of endoxifen in European patients having the cytochrome P450 (CYP) 2D6 extensive metabolizer (EM) genotype or phenotype. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day before the day on which the median trough level of the endoxifen concentration first exceeds the median trough-level endoxifen concentration in the example population consisting of European patients of the CYP2D6 EM genotype or phenotype under standard therapy, in this case, day 9.

FIG. 12 shows the result of the loading-dose control study using PK-Sim® as per the method according to the invention for the simultaneous administration of tamoxifen and endoxifen in CYP2D6 EM patients. FIG. 12 shows the trough plasma concentrations of tamoxifen (TAM), N-desmethyltamoxifen (NDM), 4-hydroxytamoxifen (4OH) and endoxifen (END) following simultaneous once daily administration of 20 mg of tamoxifen in European patients having the cytochrome P450 (CYP) 2D6 extensive metabolizer (EM) genotype or phenotype. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day on which the median trough level of the endoxifen concentration first reaches the median trough-level endoxifen concentration in the example population consisting of European patients of the CYP2D6 EM genotype or phenotype under standard therapy, in this case, day 120.

Figure 13:
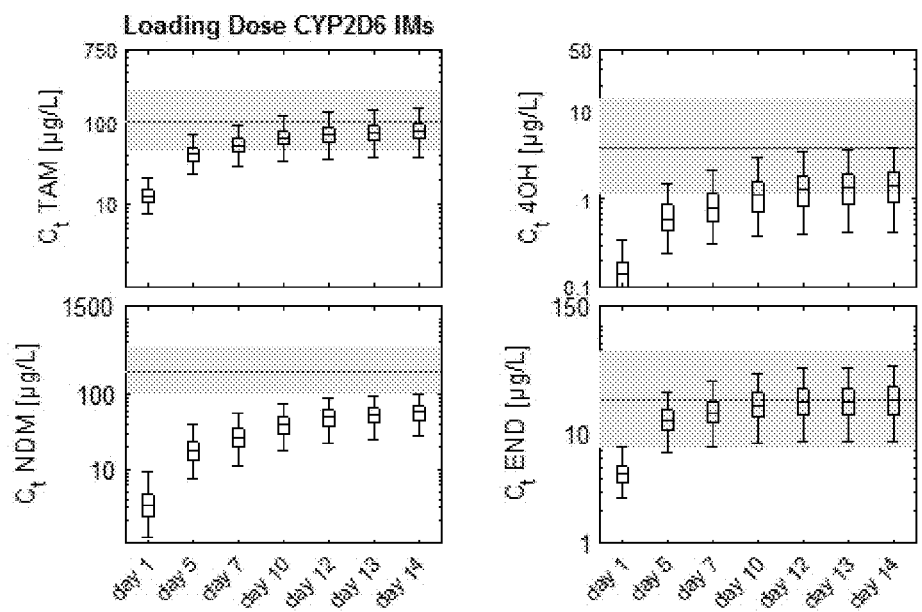
FIG. 13 shows the result of the loading dose study using PK-Sim® as per the method according to the invention for the simultaneous administration of tamoxifen and endoxifen in CYP2D6 IM patients.

FIG. 13 shows the result of the loading dose study using PK-Sim® as per the method according to the invention for the simultaneous administration of tamoxifen and endoxifen in CYP2D6 IM patients. FIG. 13 shows the trough plasma concentrations of tamoxifen (TAM), N-desmethyltamoxifen (NDM), 4-hydroxytamoxifen (4OH) and endoxifen (END) following simultaneous once daily administration of 20 mg of tamoxifen and 3 mg of endoxifen in European patients having the cytochrome. P450 (CYP) 2D6 intermediate metabolizer (IM) genotype or phenotype. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day before the day on which the median trough level of the endoxifen concentration first exceeds the median trough-level endoxifen concentration in the example population consisting of European patients of the CYP2D6 EM genotype or phenotype under standard therapy, in this case, day 13.

Figure 14:
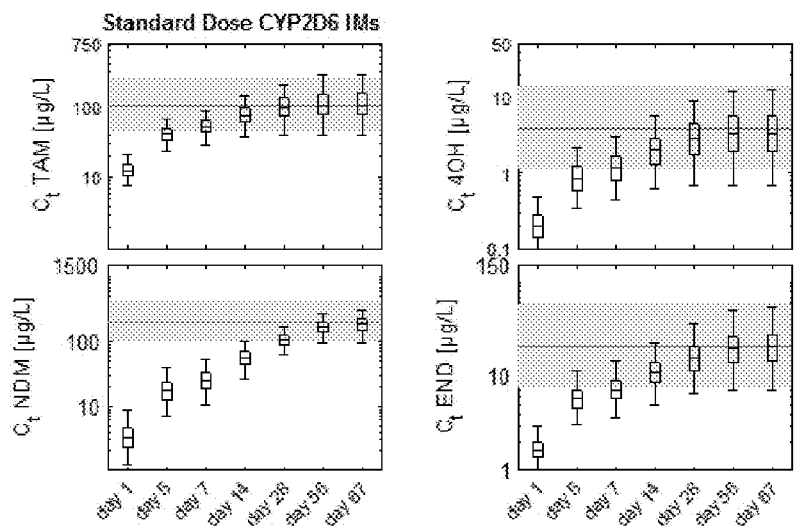
FIG. 14 shows the result of the loading-dose control study using PK-Sim® as per the method according to the invention for the simultaneous administration of tamoxifen and endoxifen in CYP2D6 IM patients.

FIG. 14 shows the result of the loading-dose control study using PK-Sim® as per the method according to the invention for the simultaneous administration of tamoxifen and endoxifen in CYP2D6 IM patients. FIG. 14 shows the trough plasma concentrations of tamoxifen (TAM), N-desmethyltamoxifen (NDM), 4-hydroxytamoxifen (4OH) and endoxifen (END) following simultaneous once daily administration of 20 mg of tamoxifen and 1 mg of endoxifen in European patients having the cytochrome P450 (CYP) 2D6 intermediate metabolizer (IM) genotype or phenotype. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day on which the median trough level of the endoxifen concentration first reaches the median trough-level endoxifen concentration in the example population consisting of European patients of the CYP2D6 EM genotype or phenotype under standard therapy, in this case, day 67.

In summary, the direct comparison between the administration of 20 mg of tamoxifen in CYP2D6 EMs or 20 mg of tamoxifen and 1 mg of endoxifen according to the invention in IMs and the administration according to the invention of 20 mg of tamoxifen and 3 mg of endoxifen in CYP2D6 EMs or IMs clearly shows that the endoxifen steady-state concentration is reached substantially faster with the administration of the FDC (consisting of 20 mg of tamoxifen and 3 mg of endoxifen), on average about 111 days or 54 days faster, than with the standard dose (consisting of 20 mg of tamoxifen for EMs and 20 mg of tamoxifen and 1 mg of endoxifen according to the invention).

Figure 15:
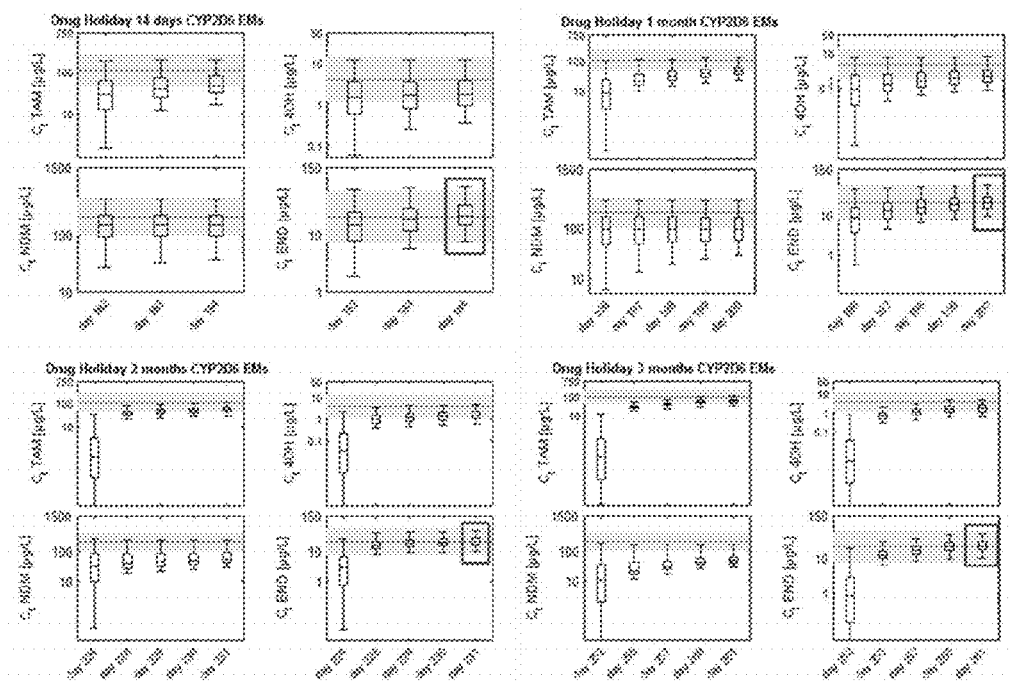
FIG. 15 shows the result of the compliance-dose study using PK-Sim® as per the method according to the invention for the simultaneous administration of tamoxifen and endoxifen in CYP2D6 EM patients.

FIGS. 15 to 18 show simulations in the investigation of non-compliance. The following scenarios were simulated:

FIG. 15 shows the result of the compliance-dose study using PK-Sim® as per the method according to the invention for the simultaneous administration of tamoxifen and endoxifen in CYP2D6 EM patients. FIG. 15 shows the trough plasma concentrations of tamoxifen (TAM), N-desmethyltamoxifen (NDM), 4-hydroxytamoxifen (4OH) and endoxifen (END) following administration of 20 mg of tamoxifen once daily for 6 months and drug holidays of 2, 4, 8 and 12 weeks in duration in European patients having the cytochrome P450 (CYP) 2D6 extensive metabolizer (EM) genotype or phenotype. This was subsequently followed by the simultaneous once daily administration of 20 mg of tamoxifen and 3 mg of endoxifen. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day before the day on which the median trough level of the endoxifen concentration first exceeds the median trough-level endoxifen concentration in the example population consisting of European patients of the CYP2D6 EM genotype or phenotype under standard therapy, in this case, day 2 after the start of FDC intake in the case of the 2-week drug holiday, day 3 after the start of FDC intake in the case of the 4-week drug holiday, day 7 after the start of FDC intake in the case of the 8-week drug holiday, and day 9 after the start of FDC intake in the case of the 12-week drug holiday.

Figure 16:
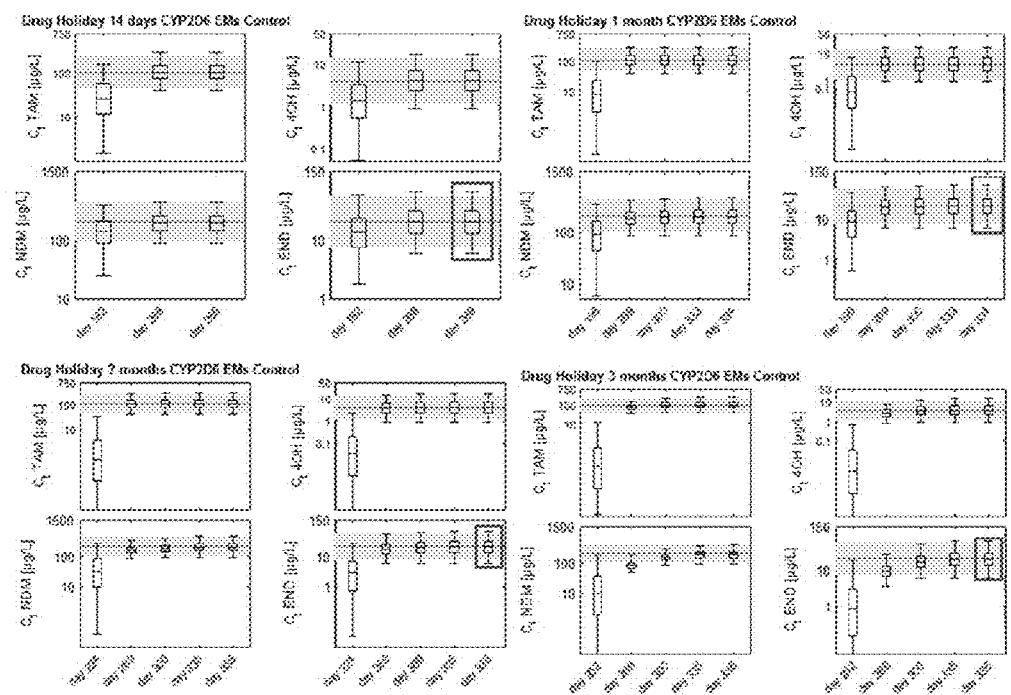
FIG. 16 shows the result of the compliance-dose control study using PK-Sim® as per the method according to the invention for the simultaneous administration of tamoxifen and endoxifen in CYP2D6 EM patients.

FIG. 16 shows the result of the compliance-dose control study using PK-Sim® as per the method according to the invention for the simultaneous administration of tamoxifen and endoxifen in CYP2D6 EM patients. FIG. 16 shows the trough plasma concentrations of tamoxifen (TAM), N-desmethyltamoxifen (NDM), 4-hydroxytamoxifen (4OH) and endoxifen (END) following administration of 20 mg, of tamoxifen once daily for 6 months and drug holidays of 2, 4, 8 and 12 weeks in duration in European patients having the cytochrome P450 (CYP) 2D6 extensive metabolizer (EM) genotype or phenotype. This was subsequently followed by the once daily administration of 20 mg of tamoxifen. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day on which the median trough level of the endoxifen concentration first reaches the median trough-level endoxifen concentration in the example population consisting of European patients of the CYP2D6 EM genotype or phenotype under standard therapy, in this case, day 269 after the start of FDC intake in the case of the 2-week drug holiday, day 334 after the start of FDC intake in the case of the 4-week drug holiday, day >336 after the start of FDC intake in the case of the 8-week drug holiday, and day >336 after the start of FDC intake in the case of the 12-week drug holiday.

Figure 17:
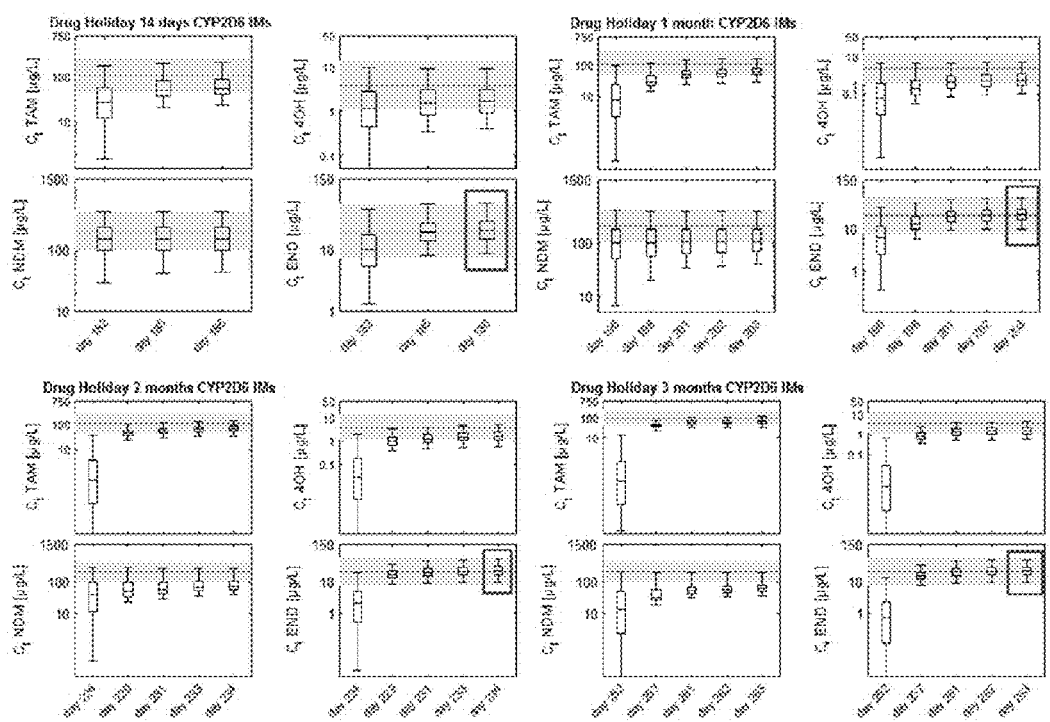
FIG. 17 shows the result of the compliance-dose study using PK-Sim® as per the method according to the invention for the simultaneous administration of tamoxifen and endoxifen in CYP2D6 IM patients.

FIG. 17 shows the result of the compliance-dose study using PK-Sim® as per the method according to the invention for the simultaneous administration of tamoxifen and endoxifen in CYP2D6 IM patients. FIG. 17 shows the trough plasma concentrations of tamoxifen (TAM), N-desmethyltamoxifen (NDM), 4-hydroxytamoxifen (4OH) and endoxifen (END) following simultaneous administration of 20 mg of tamoxifen and 1 mg of endoxifen once daily for 6 months and drug holidays of 2, 4, 8 and 12 weeks in duration in European patients having the cytochrome P450 (CYP) 2D6 intermediate metabolizer (IM) genotype or phenotype. This was subsequently followed by the simultaneous once daily administration of 20 mg of tamoxifen and 3 mg of endoxifen. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day before the day on which the median trough level of the endoxifen concentration first exceeds the median trough-level endoxifen concentration in the example population consisting of European patients of the CYP2D6 EM genotype or phenotype under standard therapy, in this case, day 4 after the start of FDC intake in the case of the 2-week drug holiday, day 7 after the start of FDC intake in the case of the 4-week drug holiday, day 10 after the start of FDC intake in the case of the 8-week drug holiday, and day 11 after the start of FDC intake in the case of the 12-week drug holiday.

Figure 18:
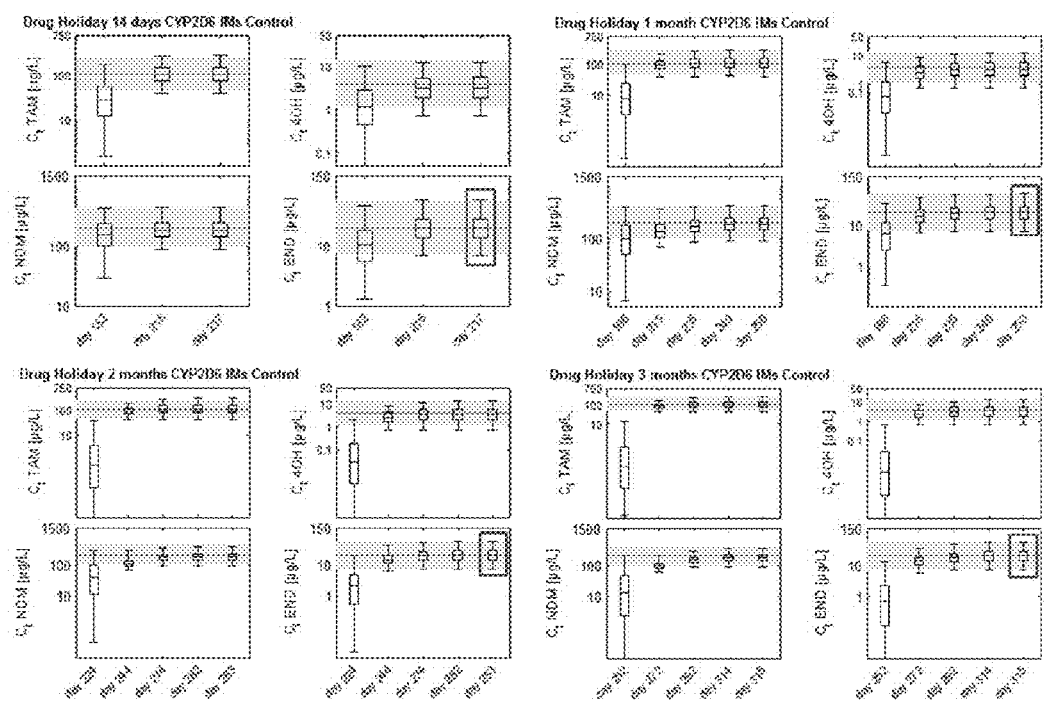
FIG. 18 shows the result of the compliance-dose control study using PK-Sim® as per the method according to the invention for the simultaneous administration of tamoxifen and endoxifen in CYP2D6 IM patients.

FIG. 18 shows the result of the compliance-dose control study using PK-Sim® as per the method according to the invention for the simultaneous administration of tamoxifen and endoxifen in CYP2D6 IM patients. FIG. 18 shows the trough plasma concentrations of tamoxifen (TAM), N-desmethyltamoxifen (NDM), 4-hydroxytamoxifen (4OH) and endoxifen (END) following simultaneous administration of 20 mg of tamoxifen and 1 mg of endoxifen once daily for 6 months and drug holidays of 2, 4, 8 and 12 weeks in duration in European patients having the cytochrome P450 (CYP) 2D6 intermediate metabolizer (IM) genotype or phenotype. This was subsequently followed by the once daily simultaneous administration of 20 mg of tamoxifen and 1 mg, of endoxifen. Serving as comparison are the pre-determined steady-state trough plasma concentrations of tamoxifen (TAM), N-desmethyltamoxifen (NDM), 4-hydroxytamoxifen (4OH) and endoxifen (END) in European patients of the CYP2D6 EM genotype or phenotype following once daily administration of 20 mg of tamoxifen over 1 year, shown as a grey band (5th-95th percentiles) with a median (dark-grey line). Taken as the time point was the day on which the median trough level of the endoxifen concentration first reaches the median trough-level endoxifen concentration in the example population consisting of European patients of the CYP2D6 EM genotype or phenotype under standard therapy, in this case, day 217 after the start of FDC intake in the case of the 2-week drug holiday, day 250 after the start of FDC intake in the case of the 4-week drug holiday, day 283 after the start of FDC intake in the case of the 8-week drug holiday, and day 315 after the start of FDC intake in the case of the 12-week drug holiday.

In summary, the simulation results from FIGS. 15 to 18 show that the fixed combined administration of 20 mg of tamoxifen and 3 mg of endoxifen is advantageous for speeding up the attainment of the effective steady-state concentrations of endoxifen in the event of non-compliance.

The invention claimed is:

1. A fixed-dose combination pharmaceutical formulation comprising:
   (A) a parent substance, the action of which is dependent on the quantity or the activity of expressed protein variants, enzyme variants, receptor variants or transporter variants, and
   (B) at least one metabolite thereof
   wherein the parent substance and the at least one metabolite are present in the pharmaceutical formulation in an amount adapted to compensate for genotype and/or phenotype differences of a patient intended to be treated with said pharmaceutical formulation, the parent substance being selected from the group consisting of tamoxifen, codeine, ezlopitant, donepezil, clopidogrel, cyclophosphamide, azathioprine, irinotecan, leflunomide, capecitabine, prasugrel, venlafaxine, losartan, tolterodine, tramadol, oxycodone, hydrocodone, doxorubicin, mycophenolate mofetil, estramustine, ifosfamide, gemcitabine, etoposide, terfenadine and methotrexate, wherein the amount of the parent substance and the amount of metabolite adapted to compensate for genotype and/or phenotype differences of a patient are calculated using a computer implemented method comprising the following:

a) inputting into an input module of an organism, of its genotype or phenotype, of the parent substance and the at least one metabolite of the parent substance, of an optimal reference steady-state plasma level for the parent substance for a reference genotype or reference phenotype in the case of delivery of the parent substance alone, b) forwarding of the data from a) into a calculation module comprising a substance data module, an organism data module, a genotype data module or phenotype data module, and a physiologically based pharmacokinetic model, wherein the substance data module comprises data concerning the physicochemical and/or biochemical properties of the substance, the organism module comprises data concerning the compartments of the organism, and the genotype data module or phenotype data module comprises genotype- or phenotype-specific data, c) automatically selecting parent substance and metabolite-specific data from the substance data module, d) automatically selecting organism-specific data from the organism data module on the basis of input a), e) automatically selecting genotype-specific or phenotype-specific data from the genotype data module or phenotype data module, f) forwarding of the selected data from a) to e) into the physiologically based pharmacokinetic model, g) calculating, by means of the physiologically based pharmacokinetic model, an optimized dosage for the parent substance for the reference genotype or reference phenotype in order to attain the inputted optimal reference plasma level for the parent substance from a), h) calculating the reference steady-state plasma level for the metabolites for the reference genotype or reference phenotype in the case of administration of the dose of parent substance calculated in g), i) calculating a plasma level of the metabolites that is reduced owing to the genotype or phenotype with respect to the corresponding reference plasma level in the case of administration of the dose of parent substance calculated in g), i) calculating the metabolite amount and a parent substance amount for the combined attainment of the reference plasma level for the metabolites from h) and of the reference plasma level for the parent substance from a), k) outputting the metabolite amount and the parent substance amount for the fixed-dose combination pharmaceutical formulation via an output module, and/or forwarding the dose calculated in j) into an automated device for dosing medicaments.

2. Formulation according to claim 1, the dosage of which is defined in a genotype- or phenotype-specific manner.

3. Formulation according to claim 1 comprising tamoxifen and endoxifen.

4. Formulation according to claim 3 comprising 15-25 mg of tamoxifen and 0.25-5.0 mg of endoxifen.

5. Formulation according to claim 4 adapted for CYP2D6 IM patients and comprising 15-25 mg of tamoxifen and 0.25-2.00 mg of endoxifen.

6. Formulation according to claim 4 adapted for CYP2D6 PM patients and comprising 15-25 mg of tamoxifen and 1.0-5.0 mg of endoxifen.

7. Formulation according to claim 4 adapted for CYP2D6 IM patients and comprising 18-22 mg of tamoxifen and 0.5-1.5 mg of endoxifen.

8. Formulation according to claim 4 adapted for CYP2D6 PM patients and comprising 18-22 mg of tamoxifen and 2.0-4.0 mg of endoxifen.

9. Formulation according to claim 1, wherein the parent substance is selected from the group consisting of tamoxifen, codeine, ezlopitant, donepezil, clopidogrel, cyclophosphamide, azathioprine, irinotecan, leflunomide, capecitabine, prasugrel, losartan, tolterodine, oxycodone, hydrocodone, doxorubicin, mycophenolate mofetil, estramustine, ifosfamide, gemcitabine, etoposide, terfenadine and methotrexate.

10. Formulation according to claim 1, wherein the parent substance is clopidogrel.

* * * * *